United States Patent [19]

Stewart

[11] Patent Number: 5,830,659
[45] Date of Patent: Nov. 3, 1998

[54] ACTIVE MICROTUBULE-BASED SEPARATIONS BY KINESINS

[75] Inventor: Russell J. Stewart, Salt Lake City, Utah

[73] Assignee: University of Utah Research Foundation, Salt Lake City, Utah

[21] Appl. No.: 713,815

[22] Filed: Sep. 13, 1996

[51] Int. Cl.[6] .............................. C12Q 1/68; C12Q 1/34; G01N 33/566; C12M 1/40
[52] U.S. Cl. ................................ 435/6; 435/7.1; 435/7.4; 435/7.5; 435/7.8; 435/18; 435/287.1; 435/287.2; 435/287.3; 435/288.4; 435/288.5; 435/317.1; 435/803; 435/814; 435/820; 530/413; 530/427
[58] Field of Search .................................. 435/7.1, 6, 7.8, 435/7.4, 7.5, 18, 287.1, 287.2, 287.3, 288.4, 288.5, 317.1, 803, 814, 820; 530/413, 427

[56] References Cited

U.S. PATENT DOCUMENTS 5,508,164   4/1996   Kausch et al. .............................. 435/6

OTHER PUBLICATIONS

Cassimeris, L.U., et al, *Dynamic Instability of Microtubules*, vol. 7, No. 4, BioEssays 149–154 (1987).

Davis, A., et al, *Purification and Biochemical Characterization of Tubulin from the Building Yeast Saccharomycyes cerevisiae*, 32 Biochemistry 8823 (1993).

Effenhauser, C., et al, *High–Speed Separation of Antisense Oligonucleotides on a Micromachined Capillary Electrophoresis Device*, vol. 66, No. 18, Analytical Chemistry, 2949–2953 (1994).

Endow, S., et al., *Mediation of meiotic and early mitotic chromosome segregation in Drosophila by a protein related to kinesin*, 345 nature 81–83 (1990).

Endow, S., et al, *Yeast Kar3 is a minus–end microtubule motor protein that destabilizes microtubules preferentially at the minus ends*, 13 EMBO J. 2708–2713 (1994).

Fan, Z.H., et al, *Micromachining of Capillary Electrophoresis Injectors and Separators on Glass Chips and Evaluation of Flow at Capillary Intersections*, 66 Anal. Chem 177–184 (1994).

(List continued on next page.)

*Primary Examiner*—Elizabeth C. Kemmerer
*Assistant Examiner*—Brian Lathrop
*Attorney, Agent, or Firm*—Thorpe, North & Western, L.L.P.

[57] ABSTRACT

A method and system for separating a selected molecule from a heterogeneous mixture of molecules in aqueous solution are described. The method comprises (a) providing a separation device comprising a loading reservoir and a receiving reservoir coupled by a channel bearing immobilized microtubules aligned parallel to the longitudinal axis thereof the channel; (b) placing an aqueous solution containing the heterogeneous mixture of molecules in the loading reservoir; (c) adding a motor-ligand composition and ATP to the aqueous solution, wherein the motor-ligand composition comprises a motor protein for attaching to microtubules and moving therealong in the presence of ATP and the ligand is capable of binding the selected molecule, such that the ligand binds the selected molecule to form a complex and the complex moves along the immobilized microtubules to the receiving reservoir; and (d) removing the selected molecule from the receiving chamber.

37 Claims, 6 Drawing Sheets

OTHER PUBLICATIONS

Jacobson, S.C., et al, *Open Channel Electrochromatography on a Microchip,* 66 Anal. Chem. 2369–2373 (1994).

Li, M., et al, *Drosophila Cytoplasmic Dynein, a Microtubule Motor That is Asymmetrically Localized in the Oocyte,* 126 The Journal of Cell Biology, 1475–1494 (1994).

Mitsui, H., et al, *Sequencing and characterization of the kinesin–related genes katB and KatC of Arabidopsis thaliana,* 25 Plant Molecular Biology, 865–876 (1994).

Pereira, A.J., et al, *Mitochondrial Association of a Plus End–Directed Microtubule Motor Expressed during Mitosis in Drosophila,* 136 The Journal of Cell Biology, 1081–1090 (1979).

Pesavento, P.A., et al, *Characterization of the KLP68D Kinesin–like Protein in Drosophila: Possible Roles in Axonal Transport,* 127 The Journal of Cell Biology, 1041–1048 (1994).

Sawin, K.E., et al, *Mitotic spindle organization by a plus–end–directed microtubule motor,* 359 Nature 540–542 (1992).

Stewart, R.J., et al, *Identification and partial characterization of six members of the kinesin superfamily in Drosophila,* 88 Proc. Natl. Acad. Sci., 8470–8474 (1991).

Uyeda, T.Q.P., et al, *Myosin Step Size Estimation from Slow Sliding Movement of Actin Over Low Densities of Heavy Meromyosin,* 214 J. Molec. Biol. 699–710 (1990).

Vale, R.D., et al, *Identification of a Novel Force–Generating Protein, Kinesin, Involved in Microtubule–Based Motility,* 42 Cell 39–50 (1985).

Wang, S., et al, *Chromokinesin: a DNA–binding, Kinestin–like Nuclear Protein,* 128 The Journal of Cell Biology 761–768 (1995).

Yang, J.T., et al, *A Three–Domain Structure of Kinestin Heavy Chain Revealed by DNA Sequence and Microtubule Binding Analyses,* 56 Cell 879–889 (1989).

Yang, J.T., et al, *Evidence That the Head of Kinesin is Sufficient for Force Generation and Motility in Vitro,* 249 Science 42–47 (1990).

Young, E.C., et al, *Subunit Interactions in Dimeric Kinesin Heavy Chain Derivatives That Lack the Kinesin Rod,* 270 The Journal of Biological Chem 3926–3931 (1995).

Berliner et al. Microtubule movement by a biotinated kinesin bound to a streptavidi–coated surface. The Journal of Biological Chemistry. vol. 269. No. 11, pp. 8610–8615, Mar. 18, 1994.

Berliner et al. Failure of a single–headed kinesin to track parallel to microtubule protofilaments. Nature. vol. 373, pp. 718–721, Feb. 23, 1995.

Endow. The emerging kinesin family of microtubule motor proteins. Trends in Biochemical Sciences, vol. 16, pp. 221–225, Jun. 1991.

Gelles et al. Structural and functional features of one– and two–headed biotinated kinesin derivatives. Biophysical Journal. vol. 68, pp. 276s–282s, Apr. 1995.

Stewart et al. Direction of microtubule movements is an intrinsic property of the motor domains of kinesin heavy chain and Drosophila ncd protein. Proceedings of the National Academy of Sciences, USA. vol. 90, pp. 5206–5213, Jun. 1993.

Vale etal. Direct observations of single kinesin molecules moving along microtubules. Nature. vol. 380, pp. 451–453, Apr. 4, 1996.

Gittes et al. Directional loading of the kinesin motor molecule as it buckles a microtubule. Biophysical Journal. vol. 70, pp. 418–429, Jan. 1996.

Lombillo et al. Minus–end–directed motion of kinesincoated microspheres driven by microtubule depolymerization. Nature. vol. 373, pp. 161–163., Jan. 12, 1995.

ACTIVE MICROTUBULE-BASED SEPARATIONS BY KINESINS

BACKGROUND OF THE INVENTION

This invention relates to a method and system for separating a selected molecule from a heterogeneous mixture of molecules. More particularly, the invention relates to separating a selected molecule from a heterogeneous mixture of molecules by reversibly coupling the selected molecule to a motor protein such that the motor protein can transport the selected molecule away from the heterogeneous mixture by moving on microtubules immobilized in a separation device.

One of the fundamental processes occurring in biological cells is active transport on a sub-micrometer scale. The simplest eukaryotic cell contains thousands of components that must be processed, packaged, sorted, and delivered to specific locations at specific times within the cell. These essential transport processes are carried out by motor proteins that travel along microtubules reaching into every corner of the cell. Motor proteins can be conceptualized as biological machines that transduce chemical energy into mechanical forces and motion.

The motor protein, kinesin, was discovered in 1985 in squid axoplasm. R. D. Vale et al., Identification of a Novel Force-generating Protein, Kinesin, Involved in Microtubule-based Motility, 42 Cell 39–50 (1985). In the last few years, it has been discovered that kinesin is just one member of a very large family of motor proteins. E.g., S. A. Endow, The Emerging Kinesin Family of Microtubule Motor Proteins, 16 Trends Biochem. Sci. 221 (1991); L. S. B. Goldstein, The Kinesin Superfamily: Tails of Functional Redundancy, 1 Trends Cell Biol. 93 (1991); R. J. Stewart et al., Identification and Partial Characterization of Six Members of the Kinesin Superfamily in *Drosophila*. 88 Proc. Nat'l Acad. Sci. USA 8470 (1991). Other motor proteins include dynein, e.g. M.-G. Li et al., *Drosophila* Cytoplasmic Dynein, a Microtubule Motor that is Asymmetrically Localized in the Oocyte, 126 J. Cell Biol. 1475–1493 (1994), and myosin, e.g. T. Q. P. Uyeda et al., 214 J. Molec. Biol. 699–710 (1990). Kinesin, dynein, and related proteins move along microtubules, whereas myosin moves along actin filaments. It has now become apparent that eukaryotic cells use motor proteins to mediate numerous transport requirements. In addition to its motor activity, kinesin is also a microtubule-activated adenosine triphosphatase (ATPase).

Kinesin is composed of two heavy chains (each about 120 kDa) and two light chains (each about 60 kDa). The kinesin heavy chains comprise three structural domains: (a) an amino-terminal head domain, which contains the sites for ATP and microtubule binding and for motor activity; (b) a middle or stalk domain, which may form an α-helical coiled coil that entwines two heavy chains to form a dimer; and (c) a carboxyl-terminal domain, which probably forms a globular tail that interacts with the light chains and possibly with vesicles and organelles. Kinesin and kinesin-like proteins are all related by sequence similarity within an approximately 340-amino acid region of the head domain, but outside of this conserved region they show no sequence similarity.

The motility activity of purified kinesin on microtubules has been demonstrated in vitro. R. D. Vale et al., Identification of a Novel Force-generating Protein, Kinesin, Involved in Microtubule-based Motility, 42 Cell 39–50 (1985). Further, fulllength kinesin heavy chain and several types of truncated kinesin heavy chain molecules produced in *E. coli* are also capable of generating in vitro microtubule motility. J. T. Yang et al., Evidence that the Head of Kinesin is Sufficient for Force Generation and Motility In Vitro, 249 Science 42–47 (1990); R. J. Stewart et al., Direction of Microtubule Movement is an Intrisic Property of the Motor Domains of Kinesin Heavy Chain and *Drosophila* NCD Protein, 90 Proc. Nat'l Acad. Sci. USA 5209-5213 (1993). The kinesin motor domain has also been shown to retain motor activity in vitro after genetic fusion to several other proteins including spectrin, J. T. Yang et al., The Head of Kinesin is Sufficient for Force Generation and Motility In Vitro, 249 Science 42 (1990), glutathione S-transferase, R. J. Stewart et al., Direction of Microtubule Movement is an Intrinsic Property of the NCD and Kinesin Heavy Chain Motor Domains, 90 Proc. Nat'l Acad. Sci. USA 5209 (1993), and biotin carboxyl carrier protein, E. Berliner, Microtubule Movement by a Biotinated Kinesin Bound to a Streptavidin-coated Surface, 269 J. Biol. Chem. 8610 (1994).

Similarly, methods have been developed for manipulation of microtubules. Microtubules can be routinely reassembled in vitro from tubulin purified from bovine brains. The nucleation, assembly, and disassembly reactions of microtubules have been well characterized. L.U. Cassimeris et al., Dynamic Instability of Microtubules, 7 Bioessays 149 (1988). More recently, considerable progress has been made toward producing recombinant tubulin in yeast. A. Davis et al., Purification and Biochemical Characterization of Tubulin from the Budding Yeast Saccharomyces cerevisiae, 32 Biochemistry 8823 (1993).

Separation of selected molecules from complex mixtures of molecules is of great importance in chemical, pharmaceutical, biotechnological, health-related and medical, and many other industries. Great amounts of time and money are spent on performing such separations. There is also an interest in instrument miniaturization driven by potential for substantially decreased analysis time, decreased reagent volumes and cost, decreased analyte volumes, integration of analytical techniques in a single device, and the economy of batch fabrication of complex devices.

In view of the foregoing, it will be appreciated that providing a method of separating a selected molecule from a heterogeneous mixture of molecules by reversibly coupling the selected molecule to a motor protein for transport on microtubules immobilized in a separation device would be a significant advancement in the art.

BRIEF SUMMARY OF THE INVENTION

It is an object of the present invention to provide a method for separating a selected molecule from a heterogeneous mixture of molecules.

It is also an object of the invention to provide a method for separating a selected molecule from a heterogeneous mixture of molecules by reversibly coupling the selected molecule to a motor protein, which transports the selected molecule on immobilized microtubules.

It is another object of the invention to provide a microfabricated device comprising immobilized microtubules for performing separations using a motor protein reversibly coupled to a selected molecule to be isolated.

It is still another object of the invention to provide a separation system that recognizes, separates, and detects selected molecules on a single micromachined chip.

These and other objects are accomplished by providing a method for separating a selected molecule from a heterogeneous mixture of molecules comprising:

(a) providing a separation device comprising a loading reservoir and a receiving reservoir coupled by a channel having immobilized to a surface thereof a plurality of microtubules aligned substantially parallel to a longitudinal axis of the channel;

(b) placing an aqueous solution comprising the heterogeneous mixture of molecules in the loading reservoir;

(c) adding a motor-ligand composition and an effective amount of ATP to the aqueous solution, wherein the motor-ligand composition comprises (i) a motor protein capable of attaching to the immobilized microtubules and moving therealong in the presence of ATP as a source of chemical energy, and (ii) a ligand coupled to the motor protein, wherein the ligand is capable of selectively binding the selected molecule, such that the ligand selectively binds the selected molecule and the motor protein attaches to the immobilized microtubules and transports the bound selected molecule therealong to the receiving reservoir; and (d) removing the selected molecule from the receiving reservoir.

Preferably, the motor protein comprises the N-terminal 410 amino acid residues of kinesin. In one illustrative embodiment, the ligand comprises an oligonucleotide having a nucleotide sequence capable of hybridizing to a target site on the selected molecule. A preferred oligonucleotide has a nucleotide sequence capable of hybridizing to a phage λ cos site, wherein the target site comprises a phage λ cos site. In another preferred embodiment, the ligand comprises an oligonucleotide and the method further comprises providing an adaptor oligonucleotide comprising a first hybridization site and a second hybridization site, wherein the ligand is capable of hybridizing to the first hybridization site and the second hybridization site is capable of hybridizing to a target site on the selected molecule.

In another preferred embodiment, the ligand comprises a peptide, such as streptavidin, protein A, or an immunoglobulin such as a single chain antibody. With a streptavidin, the ligand will bind any biotinylated molecule, or a biotinylated bead can be used to simultaneously bind a plurality of motor-ligand compositions and a plurality of selected molecules conjugated to streptavidin.

In another preferred embodiment, the method further comprises, prior to removing the selected molecule from the receiving reservoir, detecting the presence of the selected molecule in the receiving reservoir. For example, detection of a nucleic acid, protein, or other selected molecule can be with an appropriate fluorescent dye.

The invention also comprises aligning the microtubules in the channel of the separation device. Preferred methods of aligning the microtubules include flow alignment, nucleating with centrosomes or axoneme fragments, and fletching.

A preferred separation device is a micrometer-scale device wherein the loading reservoir, receiving reservoir, and channel are micromachined into a substrate.

Another aspect of the invention is a system for separating a selected molecule from a heterogeneous mixture of molecules in aqueous solution comprising:

(a) a separation device comprising a loading reservoir and a receiving reservoir coupled by a channel having immobilized to a surface thereof a plurality of microtubules aligned substantially parallel to a longitudinal axis of the channel;

(b) a motor-ligand composition comprising (i) a motor protein capable of attaching to the immobilized microtubules and moving therealong in the presence of ATP as a source of chemical energy, and (ii) a ligand coupled to the motor protein, wherein the ligand is capable of selectively binding the selected molecule;

(c) an effective amount of ATP for providing chemical energy to the motor protein for supporting movement thereof along the immobilized microtubules.

BRIEF DESCRIPTION OF THE SEVERAL VIEW OF THE DRAWINGS

FIGS. 6A–E show immobilization of microtubules on the surface of a microchannel in a microfabricated device according to the present invention.

Figure 7A:
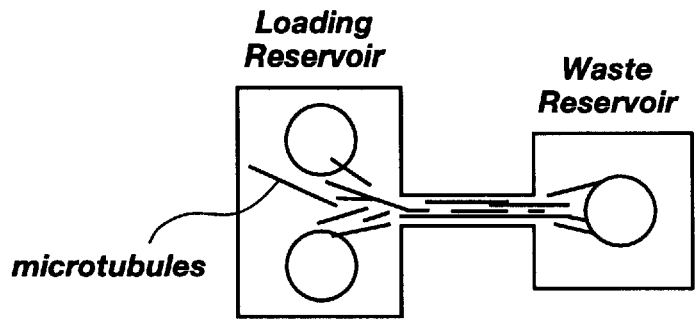
Figure 7B:
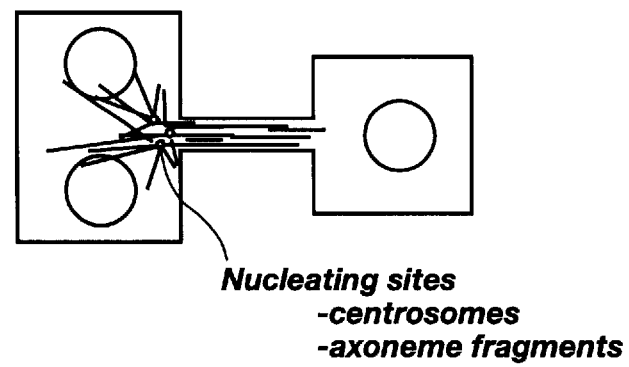
Figure 7C:
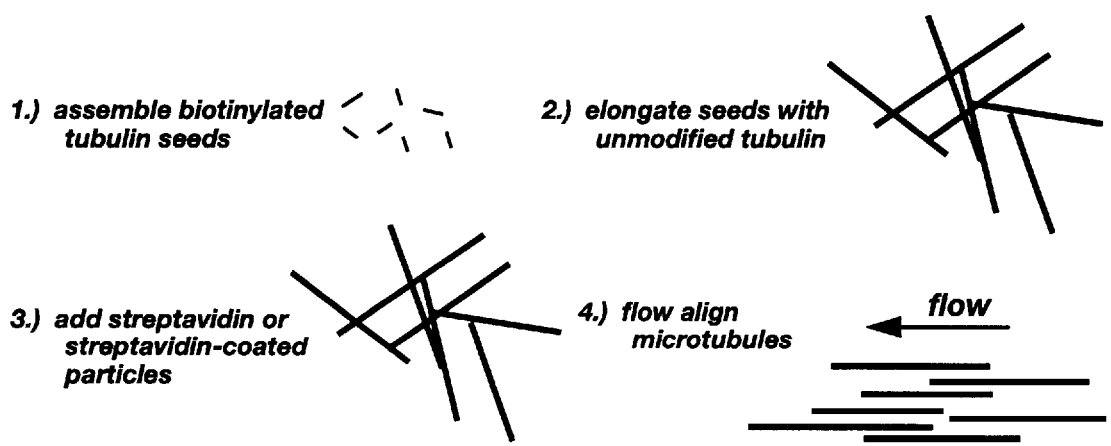

FIGS. 7A–C show, respectively, methods of aligning microtubules in the microchannel of a microfabricated device by flow alignment, nucleating with centrosomes or axoneme fragments, and fletching.

Figure 8:
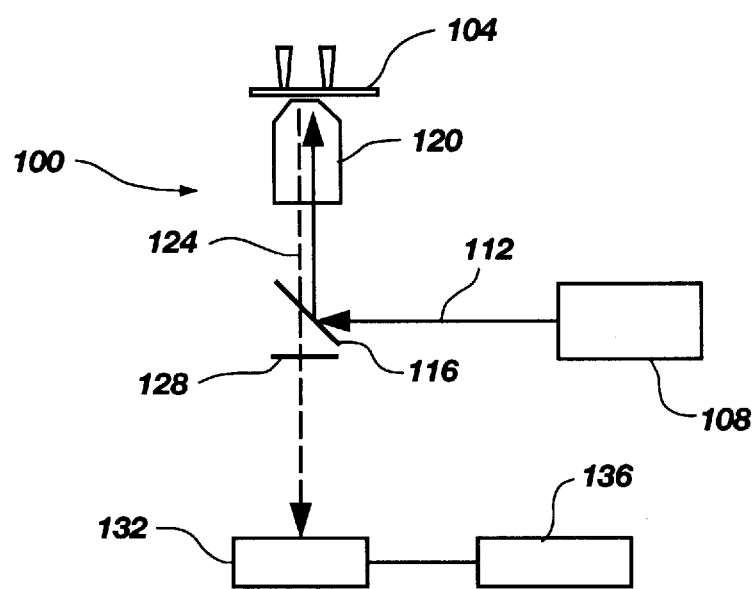

FIG. 8 shows a schematic diagram of a detection system coupled to a separation system according to the present invention.

Figure 9:
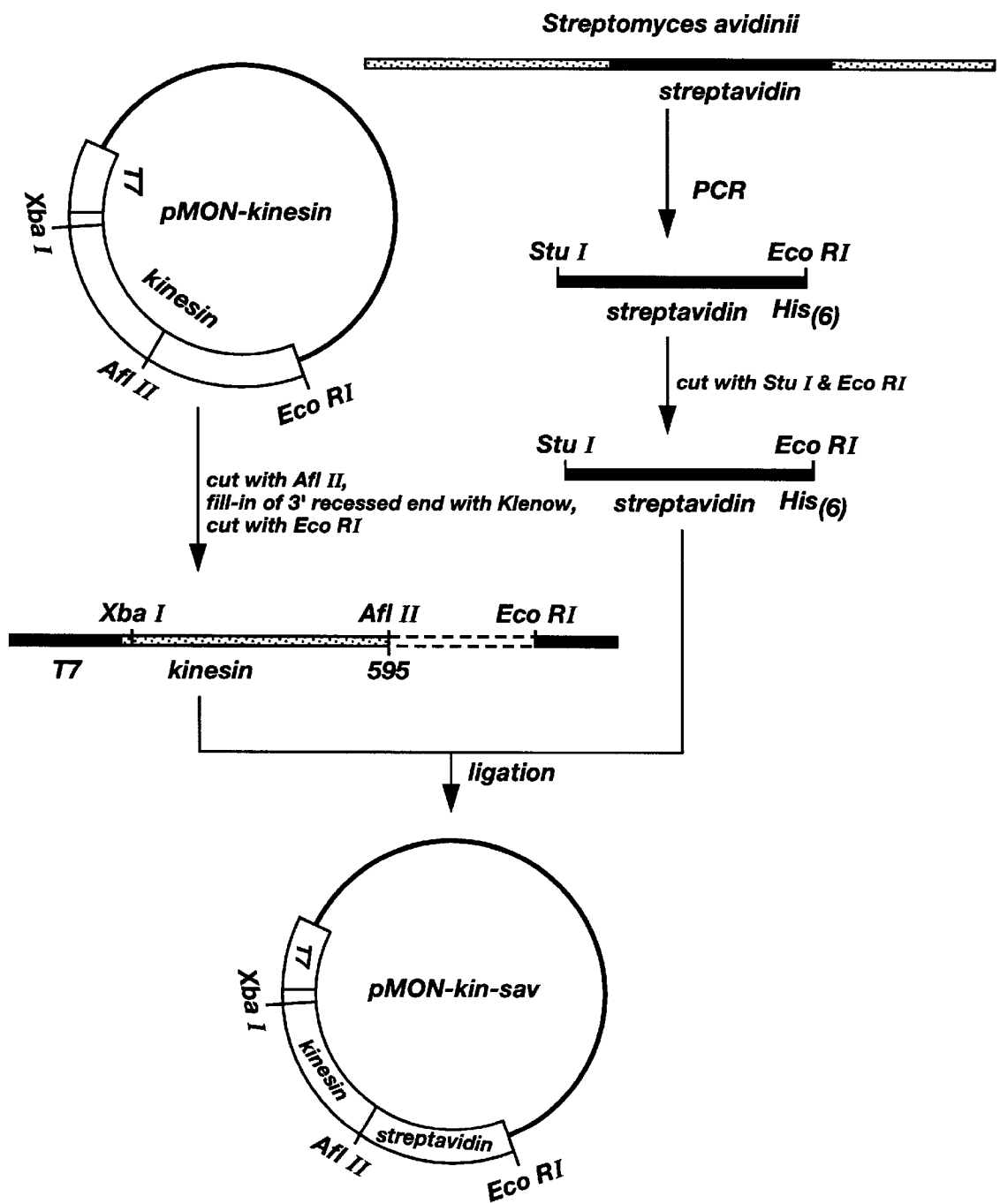

FIG. 9 shows a construction map of a plasmid, p-MONkin-sav, for expression of a kinesin-streptavidin fusion protein.

DETAILED DESCRIPTION

Before the present method and system for separating a selected molecule from a heterogeneous mixture of molecules are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a separation system containing "a microtubule" includes a system containing two or more of such microtubules, reference to "a motor-ligand composition" includes reference to two or more of such motor-ligand compositions, and reference to a separation system containing "a channel" includes reference to two or more of such channels.

In describing and claiming the present invention, the following terminology will be used in accordance with the definitions set out below.

As used herein, "micromachining," "micromachined," and similar terms refer to the processes used to create micrometer-sized structures with primarily mechanical functions on a glass, silicon, silica, or photoreactive polymer-coated chip or other suitable substrate. The processes of micromachining are based on techniques developed in the microelectronics industry to create layered structures in integrated circuits, e.g. photolithography and film deposition procedures. In a preferred embodiment of the present invention, the dimensions of a microchannel connecting a loading reservoir and a receiving reservoir are about 125 μm in length by about 25 μm in width by about 10 μm in depth, but the dimensions of such microchannels are limited only by functionality. The dimensions of the loading and receiving reservoirs are not considered to be critical and are also limited only by functionality. The microchannel is constructed of sufficient length such that the motor-ligand composition can transport a selected molecule from the loading reservoir to the receiving reservoir before contaminating molecules reach the receiving reservoir by diffusion. Kinesins move at a rate of about 60 μm/min. Diffusion of undesirable molecules can be retarded by application of an electrical field and/or increasing the viscosity of the liquid medium, and the like.

As used herein, "hybridization," "hybridizing," and similar terms refers to forming double-stranded nucleic acid molecules by hydrogen bonding of complementary base pairs, as is well known in the art. A person skilled in the art will recognize that a certain amount of mismatching is permitted under certain circumstances such that hybridization will still occur. Further, the conditions of hybridization can be manipulated by varying the lengths and GC ratios of complementary sequences that are to be hybridized, the amount of mismatching, the monovalent salt concentration, the presence of certain solvents such as formamide, and the temperature, according to principles well known in the art, such as are described in J. Sambrook et al., Molecular Cloning: A Laboratory Manual (2d ed., 1989); T. Maniatis et al., Molecular Cloning: A Laboratory Manual (1982); F. Ausubel et al., Current Protocols in Molecular Biology (1987), hereby incorporated by reference.

As used herein, "motor protein" means a protein that transduces chemical energy into mechanical forces and motion. Preferred motor proteins for the present invention are kinesin and related proteins, such as ncd, S. A. Endow et al., Mediation of Meiotic and Early Mitotic Chromosome Segregation in *Drosophila* by a Protein Related to Kinesin, 345 Nature 81–83 (1990), hereby 11 incorporated by reference, that are highly processive, i.e. do not readily detach from the microtubule tracks to which they are coupled. Once such highly processive motor proteins attach to a microtubule, there is a relatively high likelihood that they will move for many micrometers along the microtubule before becoming detached. Motor proteins such as myosin and dynein are considered unsuitable for use in the present invention because they lack high processivity. Preferred motor proteins are "double-headed," that is they are heavy chain dimers, which in part explains their processivity. Kinesin moves toward the plus-end of microtubules, whereas ncd moves toward the minus-end thereof.

As used herein, "ligand" refers to a moiety that reversibly binds a selected molecule. In coordination compound chemistry, a ligand is a molecule or anion that donates a pair of electrons to a central metal atom to form a coordinate covalent bond between the ligand and the metal atom; thus, the ligand binds the metal atom. "Ligand" is used more broadly herein to refer to any moiety that reversibly binds a selected molecule that is to be separated from a mixture of molecules. For example, a ligand can be a single-stranded nucleic acid molecule that is adapted for and is capable of hybridizing to a selected complementary nucleic acid molecule. In another illustrative example, a ligand can be an antibody, Fab, F(ab')$_2$, F(ab'), single chain antibody, or the like that is capable of binding a selected antigen. In another illustrative embodiment, a ligand can be a protein A molecule, which is capable of binding IgG molecules. In another illustrative example, a ligand can be avidin or streptavidin, which is capable of binding biotin or a biotinylated molecule of interest.

As used herein, "motor-ligand composition" refers to a motor protein coupled to a ligand molecule. The motor protein portion of the motor-ligand composition is preferably derived from kinesin, ncd, or another highly processive kinesin-related motor protein. The motor protein portion should be double-headed, therefore it will contain at least about the N-terminal 410 amino acid residues of the heavy chain protein. Amino acid residues in addition to the N-terminal 410 amino acid residues can also be present, and in this respect the length of the motor protein molecules is limited only by functionality, but preferably the motor protein chain contains no more than about 900 amino acid residues. Several illustrative constructions are exemplified herein. Recombinant motor proteins are also considered within the scope of the present invention. A few illustrative motor-ligand compositions are described herein, but it should be recognized that a person of skill in the art could easily construct additional motor-ligand compositions by recombinant DNA technology.

The ligand portion of the motor-ligand composition can be any ligand that will selectively bind to a selected molecule to be separated from a mixture of molecules, provided that the ligand can be coupled to the motor protein without destroying the ability of the ligand to bind the selected molecule or the ability of the motor protein to move on the microtubules. For example, nucleic acids and certain proteins are preferred ligands. Selected oligonucleotides can be coupled to a motor protein, as will be discussed in more detail momentarily, such that the oligonucleotide is capable of hybridizing to a selected molecule, i.e. a nucleic acid molecule, that is to be separated in the separation process. The variety of molecules that can be subject to such separations is extremely wide, as will be appreciated. By way of further example, proteins such as streptavidin, protein A, and single chain antibodies can be coupled to a motor protein for binding a wide variety of molecules. Streptavidin is known to bind biotin, thus any molecule that can be biotinylated, such as DNA and proteins, can be separated with such a ligand. Protein A is known to bind to IgG molecules. Single chain antibodies can be produced that will bind to virtually any immunogen.

Coupling of an oligonucleotide ligand to a motor protein can be by any method known in the art such that the motility of the motor protein portion and ability of the oligonucleotide to hybridize are preserved. An illustrative method of coupling an oligonucleotide to a motor protein will be exemplified below. Coupling of a motor protein to a protein or polypeptide ligand can also be carried out by known methods, such as chemical coupling or, preferably, expression of a fusion protein by recombinant DNA technology. Such recombinant DNA methods are described in the Sambrook et al., Maniatis et al., and Ausubel references. Briefly, a gene encoding a motor protein is spliced to a gene encoding a selected ligand polypeptide to form a gene fusion, and then the gene fusion is expressed in a suitable expression system such as *E. coli* or yeast to produce the motor-ligand composition, which is then purified and used in the separation system.

As used herein, "peptide" means peptides of any length and includes proteins. The terms "polypeptide" and "oligopeptide" are used herein without any particular intended size limitation, unless a particular size is otherwise stated.

As used herein, "effective amount" means an amount of a source of chemical energy, such as ATP, sufficient to permit a selected motor protein to generate mechanical force and thus move along a microtubule track. An effective amount can easily be determined by a person skilled in the art without undue experimentation.

As used herein, "ATP" means adenosine triphosphate, a mononucleotide that stores chemical energy that is used by motor proteins, such as kinesin, for producing movement.

Eukaryotic cells contain thousands of components that are sorted and distributed through specific bio-recognition and directed active transport. Numerous cellular components are synthesized, processed, and utilized in distinct cellular locations, often undergoing additional processing during transit. Families of motor proteins, which transduce chemical energy released by ATP hydrolysis into mechanical force and motion, haul these cellular components along tracks of actin or microtubule filaments to specific locations. Individual motor proteins are hitched to their specific cargo through unique recognition domains, which specify their cellular function. The specific function of kinesin is to recognize and transport a subset of neuronal vesicles from the cell body to axonal synapses. W. M. Saxton et al., Kinesin Heavy Chain Is Essential for Viability and Neuromuscular Functions in Drosophila, but Mutants Show No Defects in Mitosis, 64 Cell 1093 (1991). The present invention mimics the separation functions of kinesin in nerve cells, as will become clear from the following description.

Figure 1:
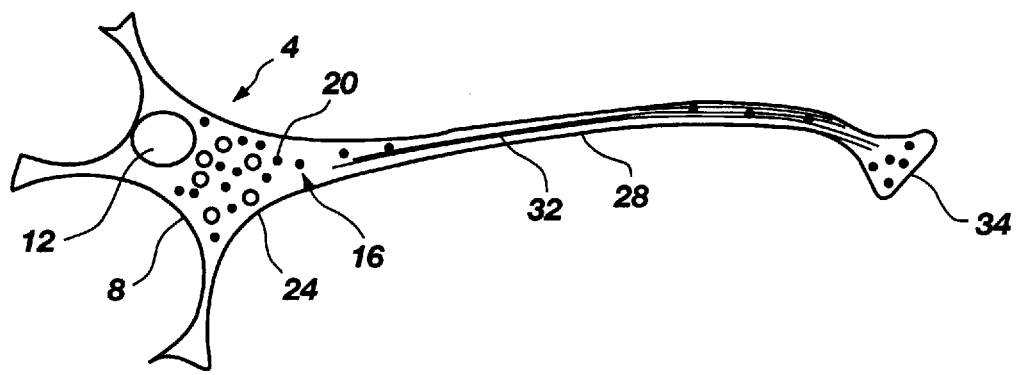
FIG. 1 shows a diagrammatic representation of a nerve cell or neuron.
Figure 2:
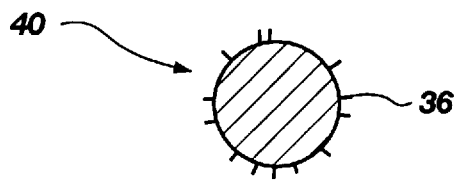
FIG. 2 shows a diagrammatic representation of a neuronal vesicle with kinesin molecules bound to the surface thereof.

FIG. 1 shows a diagrammatic representation of a nerve cell 4 or neuron comprising a cell body 8, containing a nucleus 12 and neuronal vesicles 16, 20, and 24; an axon 28, containing microtubules 32; and a synapse 34. Kinesin molecules 36 bind to a subset of neuronal vesicles 40 (FIG. 2) and transport them on microtubules through the axon. Vesicle transport can occur over distances up to a meter.

Figure 3:
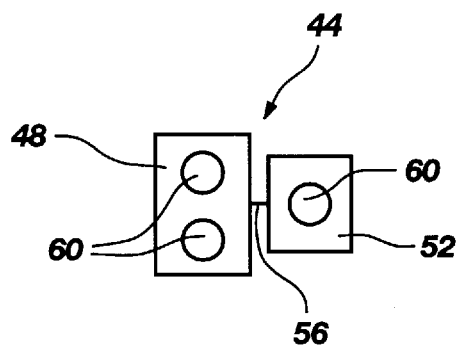
FIG. 3 shows a top schematic view of a microfabricated device according to the present invention.
Figure 4:
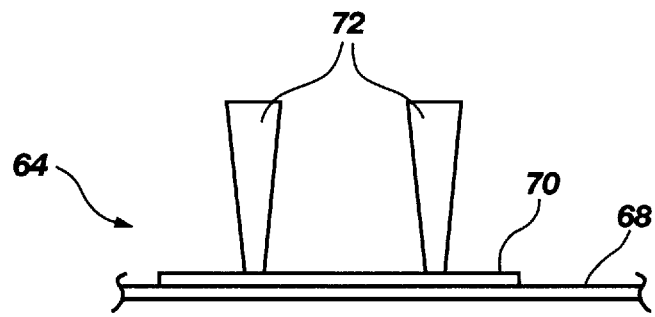
FIG. 4 shows an elevation side view of a microfabricated device according to the present invention.
Figure 5:
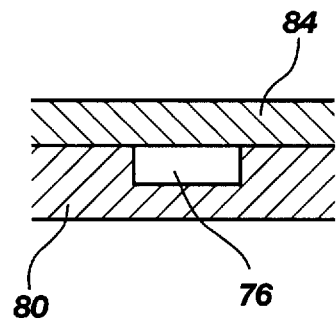
FIG. 5 shows a cross-section of the microfabricated device of FIG. 4.

FIGS. 3–5 depict an illustrative micromachined separation device according to the present invention. FIG. 3 shows a schematic diagram of a micro-fabricated device that exploits a motor protein, such as kinesin, and immobilized microtubules for recognizing, separating, and detecting a selected molecule on a single silicon chip. The device 44 comprises a loading reservoir 48 joined to a receiving reservoir 52 by a channel 56 containing immobilized microtubules. Advantageously, access ports or holes 60 are provided in the loading reservoir and receiving reservoir to permit loading of the loading reservoir and removal of separated molecules from the receiving reservoir. Microtubules are aligned and immobilized in the channel such that the long axes of the microtubules are substantially parallel to the long axis of the channel.

FIG. 4 shows an illustrative embodiment of such a microfabricated device. The device 64 comprises a substrate 68 into which are micromachined a loading reservoir, a channel, and a receiving reservoir (as best shown in FIG. 3). A coverslip or cover plate 70 is bonded to the substrate 68 to enclose the loading reservoir, channel and receiving reservoir, as will be explained in more detail momentarily. Pipet tips 72 are preferably coupled to access holes (illustrated in FIG. 3) formed in the cover plate 70 to permit access to the loading reservoir and receiving reservoir. It will be appreciated that access ports could be provide in other designs, such as through micromachining in the substrate. FIG. 5 shows a cross section through a channel 76 formed in a substrate 80 and covered or enclosed by a cover plate 84. By "enclosed" is meant that the cover plate is placed over the loading reservoir, channel, and receiving reservoir, and is preferably bonded to the substrate such that liquid placed in the loading reservoir, channel, or receiving reservoir does not leak out and such that the coverslip does not move with respect to the substrate and thus disturb the contents of the device. Thus, it is intended that the loading reservoir, channel, and receiving reservoir are in liquid communication, but that the liquid does not leak from the loading reservoir or channel into the receiving reservoir, or vice versa. The access holes permit loading and removal of solutions in the device.

Suitable materials for the substrate and cover plate include glass, silicon, silica, and the like. Any other material that would be functional for undergoing the micromachining process and would be compatible with immobilizing microtubules, the motor-ligand composition, ATP, the selected molecules to be separated, and a detection system that may be employed would also be suitable.

In another embodiment of the present invention, a detection system is coupled to the separation system previously described for monitoring the progress of separating a selected molecule from a mixture of molecules. FIG. 8 shows a schematic representation of such a detection system 100. There is shown a micromachined device 104 to which is coupled a standard epifluorescence microscope. An argon ion laser 108 emits a laser beam 112 (488 nm) that is reflected by a dichroic beam splitter 116 such that the beam passes through an objective lens 120 (Zeiss 63+, 1.4 NA) onto the microchannel of the separation device 104. A fluorescent intercalating dye, such as YOYO-1 (Molecular Probes, Eugene, Oreg.), with an excitation maximum of 491 nm and an emission maximum of 509 nm is suitable for detecting separation of DNA. The focused laser beam contacts the dye to excite fluorescence from transported DNA molecules. The fluorescence 124 is collected by the objective lens 120 and focused, and then passed through a bandpass filter 128, and onto a slit in the front of a photomultiplier tube 132. The photomultiplier tube produces a signal that is transmitted to a PC-based data acquisition system 136 (Labview, National Instruments, Inc.) for processing, quantitation, a storage.

One of the characteristics of kinesin that makes it particularly well-suited for application in a separation device is that it remains associated with the microtubule surface through thousands of ATP hydrolysis and motility cycles. J. Howard et al., Movement of Microtubules by Single Kinesin Molecules, 342 Nature 154 (1989). This means that a single kinesin molecule will move many micrometers, often completely to the end of a microtubule, without dissociating from its microtubule track. This property is likely due to cooperativity between the two motor domains of kinesin heavy chain dimers that results in one or the other of the motor domains being tightly bound at all times. D. D. Hackney, Evidence for Alternating Head Catalysis by Kinesin During Microtubule-stimulated ATP Hydrolysis, 91 Proc. Nat'l Acad. Sci. USA 6865 (1994). Myosin and dynein do not exhibit this property, but dissociate from their tracks between cycles. Microtubules are polar filaments because they are assembled from asymmetric tubulin subunits. The asymmetry is recognized by kinesin, which moves only toward what is referred to as the plus-end of the microtubules. Another member of the kinesin family, ncd, moves toward the minus-end of the microtubules.

As reviewed briefly above, the kinesin heavy chain can be divided into three domains: the motor domain (amino acid residues 1–340), the coiled-coil stalk (amino acid residues 341–800), and the tail domain (amino acid residues 801–975). The motor domain of *Drosophila kinesin* contains 5 cysteine residues. Apparently, these cysteine residues are not critical to kinesin activity since kinesin motility is not sensitive to treatment with N-ethyl maleimide. Therefore, it is possible to chemically couple a probe, such as an oligonucleotide, to cysteine residues in the kinesin stalk without disrupting kinesin motor domain function. The relevant region (amino acid residues 340–595) of the *Drosphila* kinesin stalk contains only one cysteine residue, at position 441. In initial examples of the operation of the present invention, oligonucleotide ligands are coupled to this cysteine residue. In other embodiments, a modified kinesin molecule has been constructed wherein the stalk is truncated at residue 410 and a cysteine residue is coupled thereto. In practice, the length of the kinesin molecule is limited only by functionality. Generally, however, it is advantageous to limit the size of the kinesin molecule to about 410–900 amino acid residues per chain because expression and manipulation of proteins is generally easier with smaller proteins as opposed to larger proteins. SEQ ID NO:2 contains the nucleotide sequence of the *Drosophila kinesin* gene from kinesin cDNA including the 5' untranslated region, the complete coding region up, and the 3' untranslated region. This sequence of the entire gene is set forth in J. T. Yang et al., A Three-domain Structure of Kinesin Heavy Chain Revealed by DNA Sequence and Microtubule Binding Analyses, 56 Cell 879–89 (1989), hereby incorporated by reference.

Methods have been developed for manipulation of the microtubule component of the active separation device. Microtubules can be routinely reassembled in vitro from tubulin purified from bovine brains. The nucleation, assembly, and disassembly reactions of microtubules have been well characterized over the last 20 years. L. U. Cassimeris et al., Dynamic instability of microtubules, 7 Bioessays 149 (1988).

EXAMPLE 1

In this example, standard cross-linking chemistry is used to covalently attach an oligonucleotide to the carboxy-terminus of a genetically truncated kinesin protein. Oligonucleotides can be synthesized with modified nucleotides that contain either a thiol or an amino group for crosslinking to the truncated kinesin protein. Oligonucleotides are synthesized according to methods well known in the art, such as S. A. Narang et al., 68 Meth. Enzymol. 90 (1979); E. L. Brown et al., 68 Meth. Enzymol. 109 (1979); U.S. Pat. Nos. 4,356,270; 4,458,066; 4,416,988; 4,293,652, which are hereby incorporated by reference.

The kinesin motor protein used in this example is a 441 amino acid residue genetically truncated version with an additional 6 histidine residues coupled to the C-terminal Cys residue to aid in purification (SEQ ID NO:3). This kinesin protein is expressed in *E. coli* according to methods well known in the art. This kinesin motor protein can be made by digesting pET-K447, described in J. G. Yang et al., Evidence That the Head of Kinesin Is Sufficient for Force Generation and Motility in Vitro, 249 Science 42–47 (1990), with PvuII, and then digesting with exonuclease, polishing the ends, and religating to obtain a plasmid that encodes the 441 amino acid residue kinesin. Expression of the protein is obtained by transforming *E. coli* strain BL21 (DE3), A. H. Rosenberg et al., 56 Gene 125 (1987), growing overnight cultures of the transformed bacteria, diluting the overnight culture 1:100 in LB medium, J. Miller, Experiments in Molecular Genetics, Cold Spring Harbor Laboratory, Cold Spring Harbor, N.Y. (1972), supplemented with ampicillin and shaking at 37° C. for 2 hours. The culture is then made 0.1 mM with IPTG, and shaken at 22° C. for 10 hours. The cells are then lysed for protein preparation as follows. The cells are harvested by centrifugation (SORVALL GSA rotor; 8000 rpm, 5 minutes, 4° C.). The pellet is resuspended in lysis buffer (0.1 M PIPES, pH 6.9, 1 mM $MgCl_2$, 1 mM EGTA, 2 mM dithiothreitol) and centrifuged in a weighed tube (5 minutes, 8000 rpm, SORVALL SS34 rotor, 4° C.). The pellet is weighed and resuspended in lysis buffer supplemented with the protease inhibitor phenylmethylsulfonyl fluoride (PMSF) at 1 mM. Each gram of cells is resuspended in 4 ml of buffer. The resuspended cells are lysed by sonication. The lysed cells are released into a tube sitting on ice, and centrifuged (SS34 rotor, 10,000 rpm, 30 minutes, 4° C.). The supernatant is referred to as the cell extract.

In one illustrative method, the kinesin heavy chain protein is enriched by microtubule affinity as follows. The cell extract is mixed with microtubules, prepared according to the procedure of Example 4, incubated at room temperature for 15 minutes, and centrifuged through a 2-ml sucrose cushion (15% sucrose, 20 $\mu$M taxol, 1 mM GTP in lysis buffer with 1 mM PMSF) in a swinging bucket rotor (54,000 g, 35 minutes, 22° C.). The pellet is resuspended in lysis buffer supplemented with protease inhibitor, taxol, and GTP, and centrifuged at 100,000 g. The kinesin heavy chain protein is released from microtubules by resuspending the pellet (from 1 ml of cell extract) in 100 $\mu$l of lysis buffer containing 10 mM ATP, 10 mM $MgSO_4$, and 0.1 M KCl, incubating at room temperature for 15 minutes, and centrifuging at 100,000 g for 30 minutes at 22° C. The supernatant containing enriched kinesin protein is divided into portions, frozen with liquid nitrogen, and stored at −70° C.

An alternative illustrative method of enrichment is by ammonium sulfate precipitation. The kinesin heavy chain protein is precipitated in a saturated ammonium sulfate solution (supplemented with 10 mM EDTA, adjusted to pH 8.2 with $NH_4OH$, and stored at 4° C.), which is added dropwise with constant stirring until the final concentration of ammonium sulfate is 35%. This concentration gives the best enrichment of kinesin heavy chain protein relative to other bacterial proteins. The mixture is stirred in the cold for 30 minutes, and centrifuged (SS34 rotor) at 10,000 rpm for 15 minutes. The pellet is resuspended in lysis buffer with protease inhibitors (200 $\mu$l of buffer for 10 ml of cell extract), and dialyzed in 1 liter of lysis buffer for 6 hours with one change. The dialyzed sample is clarified by centrifugation at 150,000 g for 30 minutes at 4° C.

Residue 441 of the kinesin protein is a Cys residue to which the SEQ ID NO:1 oligonucleotide is coupled. This cysteine residue of kinesin is crosslinked to a 3' amino group of the oligonucleotide using the heterobifunctional crosslinker, succinimidyl 4-[N]maleiminomethyl] cyclohexane-1-carboxylate (SMCC, Pierce Chemical Co., Milwaukee, Wis.), according to the procedures outlined by the supplier, hereby incorporated by reference. In this example, the oligonucleotide (AGGTCGCCGC CCAT-amino (SEQ ID NO:1)) is complementary to the single-stranded cos site of lambda DNA.

EXAMPLE 2

In this Example, the procedure of Example 1 is followed with the exception that the kinesin motor protein comprises the N-terminal 410 amino acid residues of the kinesin protein to which is added a C-terminal Cys residue (SEQ ID NO:4).

EXAMPLE 3

In this example, a kinesin motor protein is coupled to a streptavidin ligand according to the construction set forth in FIG. 9 and as follows. The plasmid pMON-kinesin was constructed by ligating an XbaI-EcoRI fragment containing the kinesin gene from the pET-kin plasmid into the pMON plasmid (R. J. Duronio et al., 87 Proc. Nat'l Acad. Sci. USA 1506 (1990)) that was digested with XbaI and EcoRI. The construction of pET-kin is described in J. T. Yang et al., Evidence That the Head of Kinesin Is Sufficient for Force Generation and Motility in Vitro, 249 Science 42–47 (1990), hereby incorporated by reference. The pET-kin plasmid contains the entire protein coding region of the kinesin heavy chain cDNA. Proteins produced from pET-kin have an alanine residue inserted after the first methionine residue of the kinesin heavy chain and an alteration of Ala$^3$ to Arg. The PMON-kin plasmid is an expression plasmid for expression of kinesin in $E.\ coli$ under the control of a T7 promoter. This plasmid is digested with the restriction endonuclease AflII, the 3' recessed ends are filled in with the Klenow fragment of $E.\ coli$ DNA polymerase I, and then the resulting blunt-ended plasmid is digested with EcoRI. $Streptomyces\ avidinii$ DNA was purified from an $S.\ avidinii$ culture (ATCC no. 27419) according to methods well known in the art, e.g. Sambrook et al., supra; Maniatis et al., supra; and Ausubel, supra. A portion of $S.\ avidinii$ DNA containing the streptaviding gene was amplified by polymerase chain reaction (PCR) with the primers described below according to methods well known in the art, for example, U.S. Pat. No. 4,683,195; U.S. Pat. No. 4,683,202; U.S. Pat. No. 4,800,159; U.S. Pat. No. 4,965,188; PCR Technology: Principles and Applications for DNA Amplification (H. Erlich ed., Stockton Press, New York, 1989); PCR Protocols: A Guide to Methods and Applications (Innis et al. eds, Academic Press, San Diego, Calif., 1990), hereby incorporated by reference. The coding primer is identified as SEQ ID NO:5, having a sequence of GAAGGCCTTG ACCCCTCCAA GGACTC. The non-coding primer is identified herein as SEQ ID NO:6, having a sequence of GGAATTCAAT GATGATGATG ATGATGCTGA ACGGCGTCGA. This non-coding primer introduces six consecutive histidine codons, a stop codon, and an EcoRI site at 3' end of the streptaviding gene. The amplified DNA was then digested with restriction endonucleases StuI and EcoRI, and the resulting fragment was ligated into the digested pMON-kinesin plasmid with T4 ligase. Restriction endonuclease digestions and ligase reactions were performed according to procedures well known in the art, e.g., J. Sambrook et al., Molecular Cloning: A Laboratory Manual (2d ed., 1989); T. Maniatis et al., Molecular Cloning: A Laboratory Manual (1982); F. Ausubel et al., Current Protocols in Molecular Biology (1987), hereby incorporated by reference. The resulting plasmid is designated pMON-kin-sav and comprises a gene fusion of kinesin, truncated at amino acid 595, with streptavidin. Expression of this plasmid in $E.\ coli$ results in a kinesin-streptavidin fusion protein.

This fusion protein is purified from bacterial cells according to the method of Example 1 except the cell extract is purified by a one-step immobilized metal affinity chromatography step instead of by microtubule affinity or ammonium sulfate enrichment. The six consecutive histidine residues at the C-terminus of the kinesin/streptavidin fusion protein have an affinity for a nickel-charged resin (such as "PROBOND," Invitrogen, San Diego, Calif.). Thus, the cell extract is caused to pass through the nickel-charged resin such that the kinesin/streptavidin fusion protein binds to the metal atoms through the 6 His residues. The column is then washed with lysis buffer to remove other bacterial proteins, and the kinesin/streptavidin fusion protein is eluted in lysis buffer containing 250 mM imidizole. The eluted protein is then desalted with SEPHADEX G-25 into PEM 80 buffer (80 mM PIPES, pH 6.9, 1 mM EGTA, 4 mM MgSO$_4$).

Streptavidin has a high affinity for biotin. Thus, this kinesin-streptavidin fusion protein is useful for separations wherein the molecule of interest, e.g. nucleic acid, protein, or other, is biotinylated. The avidin/streptavidin reaction with biotin is described in P. Langer et al., 78 Proc. Nat'l Acad. Sci USA 6633–37 (1981); A. Forster et al., 13 Nucleic Acids Res. 745–61 (1985); L. Riley et al., 5 DNA 333–37 (1986), hereby incorporated by reference.

EXAMPLE 4

In this example, there is described an illustrative method of purifying tubulin from bovine brain. Brain tissue was homogenized at 4° C. for 45 seconds at low speed in a Waring blender in 0.5 ml of polymerization buffer per gram of wet weight. The polymerization buffer (PM) is 50 mM (piperzine-N,N'-bis 2-ethanesulfonic acid)-KOH (PIPES-KOH) pH 6.9, 0.5 mM MgSO$_4$, 1 mM EGTA, 0.5 mM GTP. The resulting homogenate was centrifuged at 130,000 g for 75 minutes at 4° C. The supernatant solution was then diluted 1:1 with PM containing 8 M glycerol and incubated at 37° C. for 30 minutes to assemble microtubules. The microtubules were then sedimented at 130,000 g for 75 minutes at 25° C., and the pellet was resuspended in cold PM (about 0.2–0.25 the volume of the crude supernatant solution) using a Dounce homogenizer and incubated at 4° C. for 30 minutes. The solution was then centrifuged at 130,000 g for 30 minutes at 4° C. to sediment any remaining microtubules and aggregates not dissociated by cold treatment. The supernatant solution from this centrifugation was made 8 M in glycerol and stored for up to 3–4 days at 20° C. before use.

Typically, an appropriate aliquot of the stored tubulin solution was diluted 1:1 with PM containing 2 mm GTP and incubated at 37° C. for 39 minutes to assemble microtubules. The microtubules were collected as described above, resuspended, and depolymerized in column buffer (CB; 50 mM PIPES-KOH pH 6.9, 0.5 mM MgSO$_4$, 1 mM EGTA, 0.1 mM GTP), and incubated at 4° C. for 30 minutes to assemble microtubules. The solution was then clarified by centrifuging at 130,000 g for 30 minutes at 4° C. The supernatant from this centrifugation was designated as 2X-microtubule protein.

Phosphocellulose (Whatman P11) was precycled by suspending it in 0.5 N KOH for 30 minutes (1 g phosphocellulose/15 ml); the exchanger was allowed to settle, the supernatant decanted, and the phosphocellulose washed with distilled water until the effluent was pH 8. The exchanger was then suspended in 0.5 N HCl for 30 minutes (1 g/15 ml), the supernatant decanted, and this step repeated. The phosphocellulose was then washed with distilled water until the effluent was near neutrality, suspended in 50 mM PIPES-KOH (pH 6.9), and stored at 4° C. until use.

Phosphocellulose columns, 25×1.5 cm, were equilibrated by washing with Cs; 2X-microtubule protein (3 mg protein/ml bed volume) was run into this column. The tubulin flows through the phosphocellulose column without binding, thus the flow-through solution containing tubulin was collected, GTP was added to 0.1 mM, and then the tubulin was frozen with liquid nitrogen and stored at −80° C. If desired, protein was quantitated by the method of M. Bradford, A Rapid and Sensitive Method for the Quantitation of Microgram Quantities of Protein Utilizing the Principle of Protein Dye Binding, 72 Anal. Biochem. 248–54 (1976).

Microtubules were assembled as described above using phosphocellulose-purified tubulin with 2 mM GTP and at least about 40 $\mu$M taxol.

EXAMPLE 5

In this example, there is described an illustrative method of micromachining a device for separating selected molecules according to the present invention. Micromachining is carried out according to procedures well known in the art, i.e. photolithographical processes, for etching micrometer-scale channels into glass, particularly procedures used for microchannel electrophoresis applications, such as are described in A. T. Wooley & R. A. Mathies, Ultra-high-speed DNA Fragment Separations Using Microfabricated Capillary Array Electrophoresis Chips, 91 Biophysics 11348–52 (1994); C. S. Effenhauser et al., High-speed Separation of Antisense Oligonucleotides on a Micromachined Capillary Electrophoresis Device, 66 Anal. Chem. 2949 (1994); C. Effenhauser et al., 65 Anal. Chem. 2637 (1993); Z. H. Fan & D. J. Harrison, Micromachining of Capillary Electrophoresis Injectors and Separators on Class Chips and Evaluation of Flow at Capillary Intersections, 66 Anal. Chem. 177–84 (1994); W. H. Ko et al., in Sensors: A Comprehensive Survey, T. Grandke, W. H. Ko, eds., VCH Press: Weinhein, Germany, Vol. 1, pp. 107–68 (1989); K. E. Petersen, 70 Proc. IEEE 420–57 (1982), which are hereby incorporated by reference. Micromachining is done at the University of Utah Hedco Microelectronics Research Laboratory.

Glass plates are cleaned ultrasonically in detergent (5% SPARKLEEN, Fisher Scientific), methanol (reagent grade), acetone (semiconductor grade, Olin Hunt, N.J.), and deionized water in an ultrasonic bath in a class 100 clean room environment. A photomask is created with the patterns of the reservoirs and channels of the separation device. The metal mask, nominally consisting of 200-Å Cr and 1000-Å Au, is evaporatively deposited under vacuum ($<10^{-6}$ Torr), and trace organics are then removed in $H_2SO_4$—$H_2O_2$. A 1.4-$\mu$m-thick positive photoresist (Waycoat HPR 504, Olin Hunt) is spin-coated on the metal with a Solitec photoresist coater-developer (3500 rpm) and then soft-baked at 110° C. for 5 min.

Photomask layout is performed on a Princess CAD system, SUN 3/160 workstation, and the master mask is manufactured by Precision Photomask (Montreal, Canada). A Quintel contact mask aligner is used to expose the photoresist, and Microposit 354 (Shipley, Newton, Mass.) is used as a developer to obtain a selected line width for channel definition. Following a hard bake at 120° C. (5 min), the metal layer is etched away with aqua regia and a commercial Cr etch (KTI Chemicals, Sunnyside, Calif.).

The photoresist is not removed from the remaining metal layer, so as to reduce the impact of pinholes in the metal. The exposed glass is etched in a slowly stirred mixture of concentrated HF—$HNO_3$—$H_2O$ (20:14:66), or a commercial buffered oxide etch (BOE 10:1, Olin Hunt). The etch rate is determined with an Alpha-step profilometer (Tencor, Ind., Mountain View, Calif.), and the channel depth is then controlled by timing the etch period. The photoresist and metal masks are then removed with the etches described above.

The etched glass plate is then cut into individual dies of selected size using a Model 1100 wafer saw (Microautomation, Fremont, Calif.) with a spindle speed of 20,000 rpm, cutting speed of 0.64 mm/s, and a depth increment of 0.51 mm.

The etched plate and cover plate are cleaned as described above, aligned under a microscope, and thermally bonded in a Model 6-525 programmable furnace (J. M. Ney Co., Yucaipa, Calif.). The temperature program is as follows: 40° C./min to 550° C. for 30 min total, 20° C./min to 610° C. for 30 min, 20° C./min to 635° C. for 30 min, and 10° C./min to 650° C. for 6 h, followed by natural cooling of the furnace to room temperature. Unbonded regions are evidenced by interference fringes and differences in optical clarity. The bonding cycle is repeated once or twice with weights (~90 g) placed over the bonded regions. References relating to bonding of the cover plate to the substrate plate are as follows: S. C. Jacobson et al., 66 Anal. Chem. 1107 (1994); D. J. Harrison et al., 64 Anal. Chem. 1926–32 (1992), which are hereby incorporated by reference. Prior to bonding, the cover plate is drilled ultrasonically with about 0.5-mm holes to provide channel access points. Pipet tips are glued into these holes, as shown in FIG. 4. Fluid is added and withdrawn from the reservoir through the access holes with microsyringes.

EXAMPLE 6

Figure 6A:
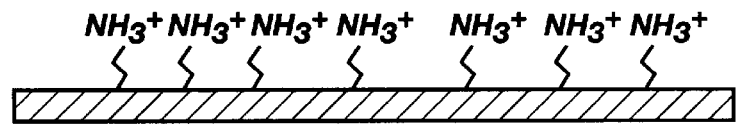
Figure 6B:
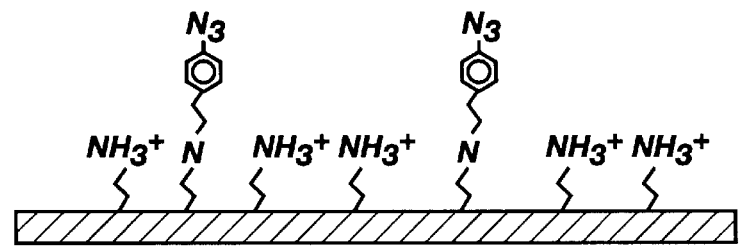
Figure 6C:
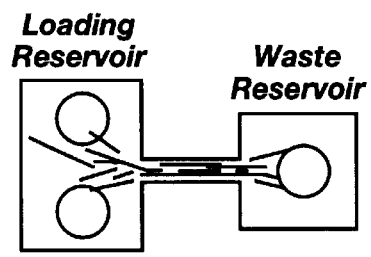
Figure 6D:
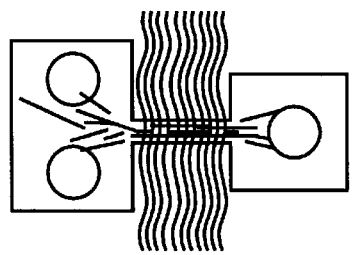
Figure 6E:
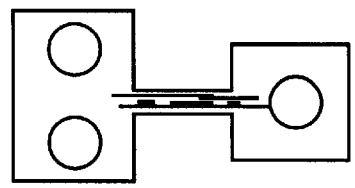

In this example, a method of immobilizing and aligning microtubules in the microchannel of a micromachined device according to Example 5 is illustrated. It is desirable to immobilize microtubules only at the entrance to and within the microchannel of the device while minimizing the number of microtubules immobilized in the loading reservoir. Immobilizing microtubules in the loading reservoir reduces the efficiency of active separation. To immobilize microtubules only in the microchannel, the surfaces of the microchannel are derivatized, and then the microtubules are bonded to the derivatized surfaces, as illustratively shown in FIGS. 6A–E. In an illustrative embodiment of this procedure, the channel surfaces are covalently derivatized with amino-silane (1% trimethoxysilylpropyldiethylenetriamine, United Chemical Tech.), FIG. 6A. A fraction of the surface amine groups is then activated for photo-crosslinking with low concentrations of sulfosuccinimidyl-(4-azidosalicylamido)-hexanoate (Pierce Chemical Co.), a heterobifunctional crosslinker that has an amine-reactive group at one end thereof and a photoactivatable azido group at the other end thereof, FIG. 6B. Microtubules reassembled in vitro from purified cow brain tubulin have a net negative surface charge at neutral pH and can be immobilized on positively charged amino-silanized surfaces (FIG. 6C), as described in K. Svoboda et al., Direct Observation of Kinesin Stepping by Optical Trapping Interferometry, 365 Nature 721 (1993), which is hereby incorporated by reference. Microtubules are strongly bound by electrostatic interactions at physiological pH and ionic strength, but can be exchanged off the positively charged surface with moderately high salt concentrations (300–500 mM KCl). Thus, the electrostatically bound microtubules are selectively and covalently immobilized in the microchannel by irradiation of the microchannel with a UV microbeam to covalently crosslink the microtubules to the amino-silanized surfaces, FIG. 6D. Uncrosslinked microtubules in the reservoirs are then washed out with a solution of moderately high salt concentration, such as 0.5 M KCl, as shown in FIG. 6E.

In this example, the microtubules are aligned in the channel by flow alignment prior to immobilization (FIG. 7A). Flow alignment is the simplest method of aligning microtubules in the channel. Because microtubules are rod-shaped, the process of flowing a microtubule solution through the device causes the microtubules to align in the microchannel. Thus, a solution containing microtubules is loaded into the loading reservoir through the loading port. The solution flows throught the channel, aligning the microtubules parallel to the longitudinal axis of the channel. A consequence of simple flow alignment is that the microtubules are aligned with random polarities.

EXAMPLE 7

In this example, the procedure of Example 6 is followed, with the exception that alignment of the microtubules is by nucleated assembly inside the device (FIG. 7B). During in vitro reassembly of microtubules, microtubules are assembled with their plus-ends distal to isolated centrosomes or axonemal fragments. Thus, use of such centrosomes or axonemal fragments as nucleating sites for microtubule assembly, wherein such centrosomes or axonemal fragments are immobilized in the loading reservoir, results in microtubules assembling in parallel orientation through the channel with the plus-ends distal to the nucleating sites.

EXAMPLE 8

In this example, the procedure of Example 6 is followed, except that alignment of the microtubules is accomplished with the use of fletchings (FIG. 7C). Biotin-labeled tubulin seeds are used to nucleate microtubule assembly with unmodified tubulin. Fletchings of streptavidin or streptavidin-coated particles orient the microtubules in parallel as they flow through the channel of the device.

EXAMPLE 9

In this example, separation of a selected nucleic acid molecule in a heterogeneous mixture of nucleic acid molecules is illustrated. A miniature separation device with immobilized microtubules is prepared according to the procedures of Examples 5 and 6. A solution containing a mixture of phage λ DNA and pBR322 plasmid DNA is placed in the loading reservoir of the device in a buffer comprising 50 mM MgSO$_4$, 50 mM ATP, 0.1 M PIPES, pH 6.9, 2.5 mM MgSO$_4$, 0.5 mM EDTA, 5 mM EGTA, and protease inhibitors as described above. The 441 amino acid residue kinesin fragment (SEQ ID NO:3) coupled to the cos oligonucleotide (SEQ ID NO:1) prepared according to Example 1 is then added to the loading reservoir. The cos oligonucleotide (SEQ ID NO:1) hybridizes with the cos site on λ DNA to form a kinesin/cos-oligonucleotide/λ-DNA complex. The kinesin fragment of this complex attaches to the immobilized microtubules in the separation device and moves along the immobilized microtubules, resulting in a net movement of these complexes into the receiving reservoir. The pBR322 plasmid DNAs fail to hybridize to the kinesin/cos-oligonucleotide compositions, and thus are not actively transported to the receiving reservoir. There is a separation of λ DNA from pBR322 DNA because active transport of λ DNA to the receiving reservoir is more rapid than diffusion of the pBR322 DNA.

EXAMPLE 10

In this example, the procedure of Example 9 is followed except that glycerol is added to the reservoir solution to inhibit the diffusion of pBR322 DNA from the loading reservoir to the receiving reservoir.

EXAMPLE 11

In this example, the procedure of Example 9 is followed except that an electric field is applied across the reservoir solution such that the anode is at the loading reservoir and the cathode is at the receiving reservoir. Negatively charged pBR322 DNA is thus inhibited from diffusing from the loading reservoir to the receiving reservoir, but the actively-transported λ DNA is transported to the receiving reservoir.

EXAMPLE 12

In this example, the procedure of Example 9 is followed except that the loading reservoir is loaded with biotinylated microbeads, which are commercially available, instead of a mixture of DNAs, and the kinesin motor protein complex is the kinesin/streptavidin fusion protein of Example 3. A plurality of kinesin/streptavidin fusion proteins bind to each biotinylated microbead by the affinity binding of streptavidin to biotin. The kinesin motor portion of the fusion protein attaches to and moves along the immobilized microtubules from the loading reservoir to the receiving reservoir.

EXAMPLE 13

In this example, the procedure of Example 12 is followed except that the solution in the loading reservoir also contains complex of bovine serum albumin (BSA) and streptavidin. The BSA/streptavidin complex also binds to the biotinylated microbeads, thus a plurality of BSA/streptaviding complexes are actively transported from the loading reservoir to the receiving reservoir along with the biotinylated microbeads. This example shows that multiple selected molecules can be separated from other molecules per kinesin motor protein according to the present invention.

---

I claim:

1. A method for separating a selected molecule from a mixture of molecules comprising:
   (a) providing a separation device comprising a loading reservoir and a receiving reservoir coupled by a channel having immobilized to a surface thereof a plurality of microtubules aligned substantially parallel to a longitudinal axis of said channel;
   (b) placing an aqueous solution comprising said mixture of molecules in said loading reservoir;
   (c) adding a motor-ligand composition and an effective amount of ATP to said aqueous solution, wherein said motor-ligand composition comprises
      (i) a processive motor protein capable of attaching to said immobilized microtubules and moving thereal ong in the presence of ATP as a source of chemical energy, and
      (ii) a ligand coupled to said motor protein, wherein said ligand is capable of selectively binding said selected molecule,
   such that said ligand selectively binds said selected molecule and said motor protein attaches to said immobilized microtubules and transports said bound selected molecule therealong to said receiving reservoir; and
   (d) removing said selected molecule from said receiving reservoir.

2. The method of claim 1 wherein said motor protein comprises the N-terminal 410 amino acid residues of *Drosophila* kinesin.

3. The method of claim 2 wherein said motor protein is a member selected from the group consisting of SEQ ID NO:3 and SEQ ID NO:4.

4. The method of claim 2 wherein said ligand comprises an oligonucleotide having a nucleotide sequence capable of hybridizing to a target site on said selected molecule.

5. The method of claim 4 wherein said oligonucleotide comprises a nucleotide sequence capable of hybridizing to a phage λ cos site and said target site comprises a phage λ cos site.

6. The method of claim 5 wherein said oligonucleotide comprises SEQ ID NO:1.

7. The method of claim 2 wherein said ligand comprises an oligonucleotide and said method further comprises providing an adaptor oligonucleotide comprising a first hybridization site and a second hybridization site, wherein said ligand is capable of hybridizing to said first hybridization site and said second hybridization site is capable of hybridizing to a target site on said selected molecule.

8. The method of claim 7 wherein said ligand is SEQ ID NO:1.

9. The method of claim 2 wherein said ligand comprises a peptide.

10. The method of claim 9 wherein said ligand comprises streptavidin.

11. The method of claim 10 further comprising adding a biotinylated bead to said aqueous solution, wherein said ligand binds to said biotinylated bead and wherein said selected molecule is coupled to streptavidin such that said selected molecule also binds to said biotinylated bead by biotinstreptavidin binding.

12. The method of claim 9 wherein said ligand comprises protein A.

13. The method of claim 9 wherein said ligand comprises a single chain antibody.

14. The method of claim 1 further comprising, prior to removing said selected molecule from said receiving reservoir, detecting the presence of said selected molecule in said receiving reservoir.

15. The method of claim 14 wherein detecting the presence of said selected molecule in said receiving reservoir comprises fluorescence detection.

16. The method of claim 1 wherein said microtubules are aligned by flow alignment.

17. The method of claim 1 wherein said microtubules are aligned by nucleating with centrosomes or axoneme fragments.

18. The method of claim 1 wherein said microtubules are aligned by fletching.

19. The method of claim 1 wherein the loading reservoir, receiving reservoir, and channel are micromachined into a substrate.

20. A system for separating a selected molecule from a mixture of molecules in aqueous solution comprising:
   (a) a separation device comprising a loading reservoir and a receiving reservoir coupled by a channel having immobilized to a surface thereof a plurality of microtubules aligned substantially parallel to a longitudinal axis of said channel;
   (b) a motor-ligand composition comprising
      (i) a procesive motor protein capable of attaching to said immobilized microtubules and moving thereal ong in the presence of ATP as a source of chemical energy, and
      (ii) a ligand coupled to said motor protein, wherein said ligand is capable of selectively binding said selected molecule;
   (c) an effective amount of ATP for providing chemical energy to said motor protein for supporting movement thereof along said immobilized microtubules.

21. The system of claim 20 wherein said motor protein comprises the N-terminal 410 amino acid residues of *Drosophila* kinesin.

22. The system of claim 21 wherein said motor protein is a member selected from the group consisting of SEQ ID NO:3 and SEQ ID NO:4.

23. The system of claim 21 wherein said ligand comprises an oligonucleotide having a nucleotide sequence capable of hybridizing to a target site on said selected molecule.

24. The system of claim 23 wherein said oligonucleotide comprises a nucleotide sequence capable of hybridizing to a phage λ cos site and said target site comprises a phage λ cos site.

25. The system of claim 24 wherein said oligonucleotide comprises SEQ ID NO:1.

26. The system of claim 21 wherein said ligand comprises an oligonucleotide and said system further comprises an adaptor oligonucleotide comprising a first hybridization site and a second hybridization site, wherein said ligand is capable of hybridizing to said first hybridization site and said second hybridization site is capable of hybridizing to a target site on said selected molecule.

27. The system of claim 26 wherein said ligand is SEQ ID NO:1.

28. The system of claim 21 wherein said ligand comprises a peptide.

29. The system of claim 28 wherein said ligand comprises streptavidin.

30. The system of claim 29 further comprising a biotinylated bead, wherein said ligand binds to said biotinylated bead and wherein said selected molecule is coupled to streptavidin such that said selected molecule also binds to said biotinylated bead by biotin-streptavidin binding.

31. The system of claim 28 wherein said ligand comprises protein A.

32. The system of claim 28 wherein said ligand comprises a single chain antibody.

33. The system of claim 20 further comprising a detector for detecting the presence of said selected molecule in said receiving reservoir.

34. The system of claim 33 wherein said detector comprises means for detecting fluorescence.

35. The system of claim 20 wherein said microtubules are aligned by flow alignment.

36. The system of claim 20 wherein said microtubules are aligned by nucleating with centrosomes or axoneme fragments.

37. The system of claim 20 wherein said microtubules are aligned by fletching.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

A G G T C G C C G C   C C A T         1 4

( 2 ) INFORMATION FOR SEQ ID NO:2:

( i ) SEQUENCE CHARACTERISTICS:
        ( A ) LENGTH: 3572 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CGCACTCCAG  CGATATCGCC  ATTTGACCAA  TTCGACTTTT  GTGTCTGGTA  TAACCACAAA          60

ATTTTCACTG  CATCTTCTTA  TTTGAGCCGC  CCCCAACCCA  ATTTTCTCGA  GTGTGTCGGA         120

ATCAGCAGAG  AATCGGAACA  AAAGGGGCAA  AACGGAGTAC  CAGAATCGGC  ACAACAACAC         180

AGTGAACAGC  AGATAGTGCG  GACGATAGCG  AGTCCGTTGA  TTATCCACGT  AAACACTGAG         240

CTGCATGCGC  AGAGGTCGCG  CCCAGAGCTG  CAGAAATCCA  ACAATCTCCG  CCAGAAAGAT         300

CTATCTCCGC  CCTGTAAGCA  ATG  TCC  GCG  GAA  CGA  GAG  ATT  CCC  GCC  GAG  GAC  353
                          Met  Ser  Ala  Glu  Arg  Glu  Ile  Pro  Ala  Glu  Asp
                           1              5                              10

AGC  ATC  AAA  GTG  GTC  TGC  CGA  TTC  CGA  CCG  CTG  AAC  GAC  AGC  GAA  GAG  401
Ser  Ile  Lys  Val  Val  Cys  Arg  Phe  Arg  Pro  Leu  Asn  Asp  Ser  Glu  Glu
              15                   20                        25

AAG  GCC  GGC  TCC  AAG  TTC  GTG  GTC  AAG  TTC  CCC  AAC  AAT  GTG  GAG  GAG  449
Lys  Ala  Gly  Ser  Lys  Phe  Val  Val  Lys  Phe  Pro  Asn  Asn  Val  Glu  Glu
         30                        35                            40

AAC  TGC  ATA  TCC  ATA  GCG  GGC  AAG  GTG  TAT  TTG  TTC  GAC  AAG  GTC  TTC  497
Asn  Cys  Ile  Ser  Ile  Ala  Gly  Lys  Val  Tyr  Leu  Phe  Asp  Lys  Val  Phe
45                             50                            55

AAA  CCG  AAT  GCA  TCC  CAG  GAA  AAG  GTC  TAC  AAT  GAG  GCG  GCC  AAG  TCC  545
Lys  Pro  Asn  Ala  Ser  Gln  Glu  Lys  Val  Tyr  Asn  Glu  Ala  Ala  Lys  Ser
60                        65                         70                       75

ATT  GTT  ACG  GAT  GTC  CTG  GCC  GGG  TAC  AAT  GGA  ACG  ATA  TTC  GCA  TAT  593
Ile  Val  Thr  Asp  Val  Leu  Ala  Gly  Tyr  Asn  Gly  Thr  Ile  Phe  Ala  Tyr
              80                        85                            90

GGT  CAG  ACG  TCC  TCC  GGA  AAA  ACG  CAT  ACG  ATG  GAG  GGC  GTG  ATC  GGG  641
Gly  Gln  Thr  Ser  Ser  Gly  Lys  Thr  His  Thr  Met  Glu  Gly  Val  Ile  Gly
              95                        100                           105

GAC  TCC  GTA  AAA  CAG  GGT  ATC  ATA  CCA  CGT  ATC  GTC  AAC  GAC  ATT  TTC  689
Asp  Ser  Val  Lys  Gln  Gly  Ile  Ile  Pro  Arg  Ile  Val  Asn  Asp  Ile  Phe
              110                       115                           120

AAT  CAC  ATC  TAC  GCG  ATG  GAG  GTG  AAC  CTG  GAG  TTT  CAC  ATC  AAG  GTC  737
Asn  His  Ile  Tyr  Ala  Met  Glu  Val  Asn  Leu  Glu  Phe  His  Ile  Lys  Val
125                            130                           135

TCC  TAC  TAC  GAG  ATC  TAC  ATG  GAC  AAG  ATT  CGA  GAT  CTG  TTG  GAC  GTC  785
Ser  Tyr  Tyr  Glu  Ile  Tyr  Met  Asp  Lys  Ile  Arg  Asp  Leu  Leu  Asp  Val
140                            145                           150                 155

TCC  AAG  GTG  AAC  CTT  AGT  GTG  CAC  GAG  GAT  AAG  AAC  CGG  GTG  CCG  TAC  833
Ser  Lys  Val  Asn  Leu  Ser  Val  His  Glu  Asp  Lys  Asn  Arg  Val  Pro  Tyr
              160                       165                           170

GTC  AAG  GGC  GCT  ACG  GAA  CGG  TTC  GTC  TCG  TCG  CCG  GAG  GAT  GTT  TTC  881
Val  Lys  Gly  Ala  Thr  Glu  Arg  Phe  Val  Ser  Ser  Pro  Glu  Asp  Val  Phe
              175                       180                           185

GAG  GTG  ATC  GAG  GAG  GGC  AAA  TCC  AAT  CGT  CAC  ATC  GCT  GTG  ACA  AAC  929
Glu  Val  Ile  Glu  Glu  Gly  Lys  Ser  Asn  Arg  His  Ile  Ala  Val  Thr  Asn
              190                       195                           200

ATG  AAC  GAG  CAT  TCT  TCG  CGA  TCC  CAC  TCA  GTA  TTC  CTT  ATC  AAT  GTG  977
Met  Asn  Glu  His  Ser  Ser  Arg  Ser  His  Ser  Val  Phe  Leu  Ile  Asn  Val
         205                       210                       215

AAG  CAG  GAG  AAC  CTG  GAG  AAC  CAG  AAG  AAA  CTA  TCC  GGC  AAA  CTC  TAC  1025
Lys  Gln  Glu  Asn  Leu  Glu  Asn  Gln  Lys  Lys  Leu  Ser  Gly  Lys  Leu  Tyr
220                       225                       230                       235
```

```
CTG  GTG  GAT  TTG  GCC  GGT  TCC  GAG  AAG  GTT  TCC  AAG  ACT  GGA  GCG  GAG        1073
Leu  Val  Asp  Leu  Ala  Gly  Ser  Glu  Lys  Val  Ser  Lys  Thr  Gly  Ala  Glu
               240                      245                      250

GGA  ACC  GTT  CTT  GAT  GAA  GCC  AAG  AAC  ATC  AAC  AAG  TCG  CTG  TCG  GCC        1121
Gly  Thr  Val  Leu  Asp  Glu  Ala  Lys  Asn  Ile  Asn  Lys  Ser  Leu  Ser  Ala
               255                      260                      265

TTG  GGC  AAC  GTA  ATT  TCT  GCC  CTG  GCG  GAC  GGA  AAC  AAA  ACG  CAC  ATC        1169
Leu  Gly  Asn  Val  Ile  Ser  Ala  Leu  Ala  Asp  Gly  Asn  Lys  Thr  His  Ile
               270                      275                      280

CCC  TAC  CGT  GAT  TCC  AAG  CTA  ACG  CGC  ATC  CTG  CAG  GAG  TCG  CTG  GGA        1217
Pro  Tyr  Arg  Asp  Ser  Lys  Leu  Thr  Arg  Ile  Leu  Gln  Glu  Ser  Leu  Gly
               285                      290                      295

GGC  AAC  GCA  CGC  ACA  ACC  ATC  GTC  ATC  TGC  TGC  TCT  CCA  GCC  AGT  TTC        1265
Gly  Asn  Ala  Arg  Thr  Thr  Ile  Val  Ile  Cys  Cys  Ser  Pro  Ala  Ser  Phe
300                 305                      310                      315

AAC  GAA  TCT  GAA  ACG  AAG  TCA  ACG  CTG  GAC  TTC  GGT  CGT  AGA  GCC  AAG        1313
Asn  Glu  Ser  Glu  Thr  Lys  Ser  Thr  Leu  Asp  Phe  Gly  Arg  Arg  Ala  Lys
                    320                      325                      330

ACA  GTG  AAG  AAC  GTG  GTC  TGC  GTT  AAC  GAG  GAG  CTT  ACT  GCC  GAG  GAA        1361
Thr  Val  Lys  Asn  Val  Val  Cys  Val  Asn  Glu  Glu  Leu  Thr  Ala  Glu  Glu
               335                      340                      345

TGG  AAG  CGA  CGC  TAT  GAA  AAG  GAG  AAG  GAA  AAG  AAC  GCC  CGA  CTA  AAG        1409
Trp  Lys  Arg  Arg  Tyr  Glu  Lys  Glu  Lys  Glu  Lys  Asn  Ala  Arg  Leu  Lys
               350                      355                      360

GGT  AAG  GTG  GAG  AAG  CTG  GAG  ATC  GAG  CTT  GCG  CGC  TGG  AGA  GCG  GGT        1457
Gly  Lys  Val  Glu  Lys  Leu  Glu  Ile  Glu  Leu  Ala  Arg  Trp  Arg  Ala  Gly
          365                      370                      375

GAA  ACT  GTT  AAG  GCG  GAG  GAG  CAA  ATC  AAC  ATG  GAG  GAT  CTC  ATG  GAG        1505
Glu  Thr  Val  Lys  Ala  Glu  Glu  Gln  Ile  Asn  Met  Glu  Asp  Leu  Met  Glu
380                      385                      390                      395

GCA  AGC  ACG  CCC  AAC  CTG  GAA  GTG  GAG  GCA  GCA  CAG  ACG  GCG  GCG  GCC        1553
Ala  Ser  Thr  Pro  Asn  Leu  Glu  Val  Glu  Ala  Ala  Gln  Thr  Ala  Ala  Ala
                    400                      405                      410

GAG  GCC  GCT  TTG  GCC  GCC  CAG  CGA  ACG  GCT  CTC  GCC  AAT  ATG  TCC  GCA        1601
Glu  Ala  Ala  Leu  Ala  Ala  Gln  Arg  Thr  Ala  Leu  Ala  Asn  Met  Ser  Ala
               415                      420                      425

TCG  GTT  GCC  GTG  AAC  GAG  CAG  GCC  AGG  CTG  GCT  ACA  GAG  TGC  GAG  CGT        1649
Ser  Val  Ala  Val  Asn  Glu  Gln  Ala  Arg  Leu  Ala  Thr  Glu  Cys  Glu  Arg
               430                      435                      440

CTC  TAC  CAG  CAG  CTG  GAC  GAC  AAG  GAT  GAG  GAG  ATC  AAT  CAG  CAG  AGC        1697
Leu  Tyr  Gln  Gln  Leu  Asp  Asp  Lys  Asp  Glu  Glu  Ile  Asn  Gln  Gln  Ser
          445                      450                      455

CAG  TAC  GCC  GAG  CAG  CTC  AAG  GAG  CAG  GTG  ATG  GAG  CAG  GAG  GAA  CTC        1745
Gln  Tyr  Ala  Glu  Gln  Leu  Lys  Glu  Gln  Val  Met  Glu  Gln  Glu  Glu  Leu
460                      465                      470                      475

ATC  GCT  AAC  GCT  CGG  CGT  GAG  TAT  GAG  ACT  TTG  CAG  TCG  GAG  ATG  GCG        1793
Ile  Ala  Asn  Ala  Arg  Arg  Glu  Tyr  Glu  Thr  Leu  Gln  Ser  Glu  Met  Ala
                    480                      485                      490

CGA  ATC  CAA  CAG  GAG  AAC  GAG  TCC  GCC  AAG  GAA  GAG  GTT  AAG  GAG  GTG        1841
Arg  Ile  Gln  Gln  Glu  Asn  Glu  Ser  Ala  Lys  Glu  Glu  Val  Lys  Glu  Val
               495                      500                      505

CTC  CAA  GCT  CTC  GAA  GAG  CTG  ACT  GTA  AAC  TAC  GAC  CAG  AAA  TCC  CAG        1889
Leu  Gln  Ala  Leu  Glu  Glu  Leu  Thr  Val  Asn  Tyr  Asp  Gln  Lys  Ser  Gln
               510                      515                      520

GAG  ATC  GAT  AAC  AAG  AAC  AAG  GAT  ATC  GAT  GCC  CTC  AAC  GAG  GAG  CTG        1937
Glu  Ile  Asp  Asn  Lys  Asn  Lys  Asp  Ile  Asp  Ala  Leu  Asn  Glu  Glu  Leu
          525                      530                      535

CAG  CAG  AAG  CAG  TCT  GTG  TTC  AAC  GCC  GCC  TCC  ACA  GAG  CTA  CAG  CAG        1985
Gln  Gln  Lys  Gln  Ser  Val  Phe  Asn  Ala  Ala  Ser  Thr  Glu  Leu  Gln  Gln
540                      545                      550                      555
```

| | | | | | | | | | | | | | | | | |
|---|---|---|---|---|---|---|---|---|---|---|---|---|---|---|---|---|
| CTC | AAT | GAC | ATG | TCC | TCA | CAC | CAG | AAG | AAG | CGC | ATC | ACG | GAA | ATG | CTA | 2033 |
| Leu | Lys | Asp | Met | Ser | Ser | His | Gln | Lys | Lys | Arg | Ile | Thr | Glu | Met | Leu | |
| | | | 560 | | | | | 565 | | | | | | 570 | | |
| ACC | AAC | CTA | CTG | CGC | GAC | CTC | GGC | GAA | GTG | GGC | CAG | GCC | ATT | GCC | CCC | 2081 |
| Thr | Asn | Leu | Leu | Arg | Asp | Leu | Gly | Glu | Val | Gly | Gln | Ala | Ile | Ala | Pro | |
| | | | | 575 | | | | | 580 | | | | | 585 | | |
| GGC | GAG | TCC | AGC | ATC | GAC | CTT | AAG | ATG | AGT | GCT | CTG | GCT | GGC | ACG | GAT | 2129 |
| Gly | Glu | Ser | Ser | Ile | Asp | Leu | Lys | Met | Ser | Ala | Leu | Ala | Gly | Thr | Asp | |
| | | | 590 | | | | | 595 | | | | | 600 | | | |
| GCC | AGC | AAG | GTG | GAG | GAA | GAT | TTC | ACC | ATG | GCG | CGT | TTG | TTT | ATC | AGC | 2177 |
| Ala | Ser | Lys | Val | Glu | Glu | Asp | Phe | Thr | Met | Ala | Arg | Leu | Phe | Ile | Ser | |
| | | 605 | | | | 610 | | | | | 615 | | | | | |
| AAG | ATG | AAG | ACG | GAG | GCC | AAG | AAC | ATT | GCC | CAG | CGA | TGC | TCC | AAC | ATG | 2225 |
| Lys | Met | Lys | Thr | Glu | Ala | Lys | Asn | Ile | Ala | Gln | Arg | Cys | Ser | Asn | Met | |
| 620 | | | | | 625 | | | | | 630 | | | | | 635 | |
| GAA | ACA | CAG | CAG | GCT | GAC | TCC | AAC | AAG | AAG | ATC | TCC | GAA | TAT | GAG | AAA | 2273 |
| Glu | Thr | Gln | Gln | Ala | Asp | Ser | Asn | Lys | Lys | Ile | Ser | Glu | Tyr | Glu | Lys | |
| | | | | 640 | | | | | 645 | | | | | 650 | | |
| GAT | CTG | GGC | GAG | TAC | CGG | CTA | CTC | ATT | TCG | CAG | CAC | GAG | GCA | CGC | ATG | 2321 |
| Asp | Leu | Gly | Glu | Tyr | Arg | Leu | Leu | Ile | Ser | Gln | His | Glu | Ala | Arg | Met | |
| | | | 655 | | | | | 660 | | | | | 665 | | | |
| AAG | TCG | CTG | CAG | GAG | TCG | ATG | CGG | GAG | GCA | GAG | AAC | AAG | AAG | CGC | ACG | 2369 |
| Lys | Ser | Leu | Gln | Glu | Ser | Met | Arg | Glu | Ala | Glu | Asn | Lys | Lys | Arg | Thr | |
| | | 670 | | | | 675 | | | | | 680 | | | | | |
| CTC | GAG | GAA | CAA | ATC | GAT | TCG | CTG | CGC | GAG | GAA | TGC | GCC | AAG | CTC | AAG | 241 |
| Leu | Glu | Glu | Gln | Ile | Asp | Ser | Leu | Arg | Glu | Glu | Cys | Ala | Lys | Leu | Lys | |
| | 685 | | | | | 690 | | | | | 695 | | | | | |
| GCC | GCC | GAG | CAC | GTT | TCC | GCC | GTT | AAC | GCC | GAG | GAG | AAA | CAG | CGG | GCT | 2465 |
| Ala | Ala | Glu | His | Val | Ser | Ala | Val | Asn | Ala | Glu | Glu | Lys | Gln | Arg | Ala | |
| 700 | | | | | 705 | | | | | 710 | | | | | 715 | |
| GAG | GAG | CTG | CGC | TCC | ATG | TTC | GAT | TCT | CAG | ATG | GAC | GAG | CTA | CGC | GAA | 2513 |
| Glu | Glu | Leu | Arg | Ser | Met | Phe | Asp | Ser | Gln | Met | Asp | Glu | Leu | Arg | Glu | |
| | | | | 720 | | | | | 725 | | | | | 730 | | |
| GCC | CAC | ACC | CGG | CAG | GTG | TCC | GAG | CTC | CGG | GAC | GAA | ATT | GCC | GCC | AAG | 2561 |
| Ala | His | Thr | Arg | Gln | Val | Ser | Glu | Leu | Arg | Asp | Glu | Ile | Ala | Ala | Lys | |
| | | | 735 | | | | | 740 | | | | | 745 | | | |
| CAG | CAC | GAA | ATG | GAC | GAG | ATG | AAG | GAT | GTC | CAT | CAA | AAG | CTG | CTC | TTG | 2609 |
| Gln | His | Glu | Met | Asp | Glu | Met | Lys | Asp | Val | His | Gln | Lys | Leu | Leu | Leu | |
| | | 750 | | | | 755 | | | | | 760 | | | | | |
| GCG | CAC | CAA | CAG | ATG | ACG | GCC | GAC | TAC | GAG | AAG | GTG | CGC | CAG | GAG | GAT | 2657 |
| Ala | His | Gln | Gln | Met | Thr | Ala | Asp | Tyr | Glu | Lys | Val | Arg | Gln | Glu | Asp | |
| | 765 | | | | | 770 | | | | | 775 | | | | | |
| GCC | GAG | AAG | TCC | AGC | GAG | CTT | CAG | AAC | ATC | ATC | CTC | ACC | AAC | GAG | CGT | 2705 |
| Ala | Glu | Lys | Ser | Ser | Glu | Leu | Gln | Asn | Ile | Ile | Leu | Thr | Asn | Glu | Arg | |
| 780 | | | | | 785 | | | | | 790 | | | | | 795 | |
| CGG | GAG | CAA | GCG | CGC | AAA | GAC | CTC | AAG | GGC | CTG | GAG | GAC | ACG | GTG | GCC | 2753 |
| Arg | Glu | Gln | Ala | Arg | Lys | Asp | Leu | Lys | Gly | Leu | Glu | Asp | Thr | Val | Ala | |
| | | | | 800 | | | | | 805 | | | | | 810 | | |
| AAG | GAG | TTG | CAG | ACG | CTA | CAC | AAC | CTG | CGA | AAA | CTT | TTC | GTT | CAG | GAT | 2801 |
| Lys | Glu | Leu | Gln | Thr | Leu | His | Asn | Leu | Arg | Lys | Leu | Phe | Val | Gln | Asp | |
| | | | | 815 | | | | | 820 | | | | | 825 | | |
| CTA | CAG | CAA | CGA | ATC | CGA | AAG | AAT | GTC | GTA | AAC | GAG | GAG | AGC | GAG | GAG | 2849 |
| Leu | Gln | Gln | Arg | Ile | Arg | Lys | Asn | Val | Val | Asn | Glu | Glu | Ser | Glu | Glu | |
| | | | 830 | | | | | 835 | | | | | 840 | | | |
| GAC | GGT | GGA | TCA | CTC | GCG | CAG | AAA | CAG | AAG | ATT | TCC | TTC | TTG | GAG | AAC | 2897 |
| Asp | Gly | Gly | Ser | Leu | Ala | Gln | Lys | Gln | Lys | Ile | Ser | Phe | Leu | Glu | Asn | |
| | | 845 | | | | | 850 | | | | | 855 | | | | |
| AAC | CTC | GAC | CAG | CTG | ACC | AAG | GTG | CAC | AAG | CAA | TTG | GTG | CGG | GAC | AAC | 2945 |
| Asn | Leu | Asp | Gln | Leu | Thr | Lys | Val | His | Lys | Gln | Leu | Val | Arg | Asp | Asn | |
| 860 | | | | | 865 | | | | | 870 | | | | | 875 | |

| | | | | | | | | | | | | | | | | |
|---|---|---|---|---|---|---|---|---|---|---|---|---|---|---|---|---|
| GCC | GAT | CTG | CGG | TGC | GAG | CTG | CCC | AAG | CTG | GAG | AAG | CGT | CTA | CGC | TGT | 2993 |
| Ala | Asp | Leu | Arg | Cys | Glu | Leu | Pro | Lys | Leu | Glu | Lys | Arg | Leu | Arg | Cys | |
| | | | 880 | | | | | 885 | | | | | 890 | | | |
| ACC | ATG | GAG | CGG | GTG | AAA | GCT | CTG | GAG | ACA | GCG | CTC | AAG | GAG | GCG | AAG | 3041 |
| Thr | Met | Glu | Arg | Val | Lys | Ala | Leu | Glu | Thr | Ala | Leu | Lys | Glu | Ala | Lys | |
| | | | 895 | | | | | 900 | | | | | 905 | | | |
| GAG | GGC | GCA | ATG | CGG | GAT | CGC | AAG | CGC | TAC | CAA | TAC | GAG | GTG | GAC | CGC | 3089 |
| Glu | Gly | Ala | Met | Arg | Asp | Arg | Lys | Arg | Tyr | Gln | Tyr | Glu | Val | Asp | Arg | |
| | | 910 | | | | | 915 | | | | | 920 | | | | |
| ATC | AAG | GAG | GCG | GTG | CGA | CAG | AAG | CAT | CTG | GGC | AGA | CGT | GGC | CCA | CAG | 3137 |
| Ile | Lys | Glu | Ala | Val | Arg | Gln | Lys | His | Leu | Gly | Arg | Arg | Gly | Pro | Gln | |
| | | 925 | | | | | 930 | | | | | 935 | | | | |
| GCA | CAG | ATC | GCA | AAG | CCG | ATC | CGG | TCC | GGC | CAA | GGT | GCA | ATC | GCC | ATT | 3185 |
| Ala | Gln | Ile | Ala | Lys | Pro | Ile | Arg | Ser | Gly | Gln | Gly | Ala | Ile | Ala | Ile | |
| 940 | | | | | 945 | | | | | 950 | | | | | 955 | |
| CGT | GGT | GGT | GGC | GCC | GTT | GGA | GGA | CCA | TCC | CCG | CTG | GCC | CAG | GTT | AAT | 3233 |
| Arg | Gly | Gly | Gly | Ala | Val | Gly | Gly | Pro | Ser | Pro | Leu | Ala | Gln | Val | Asn | |
| | | | | 960 | | | | | 965 | | | | | 970 | | |

| | | | | |
|---|---|---|---|---|
| CCT GTC AAC TCG | TAGATCCAAT | CACCACCTGT | CGCCGCCAG | TTCAGCTCCG | 3285 |
| CTTTAAACTA | AACTAGTTAT | ACATACTTAA | CATAACTGAT | AATTGCCTTC GCTTAGATGA | 3345 |
| GATGTGTCGC | GATCATGTGC | AGCGCTTTAA | ATATACATAC | ATATAATTTA ATTAAATAAA | 3405 |
| TGAAAGGAAA | CCGGAAATTA | ACTAAATTTT | ACAAACCGAA | AATAATAAAA CCCACAGATA | 3465 |
| TGTAAGGACA | TCTATATACG | TTAAGAGTAT | TTATAAACTT | TCAAACATA AACCTAAATA | 3525 |
| AAAGTCGCAG | ACAAAAAAAA | AAAAAAAAAA | AAAAAAAAAA | AAAAAA | 3572 |

( 2 ) INFORMATION FOR SEQ ID NO:3:

( i ) SEQUENCE CHARACTERISTICS:
        ( A ) LENGTH: 441 amino acid residues
        ( B ) TYPE: amino acid
        ( D ) TOPOLOGY: linear ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Ser | Ala | Glu | Arg | Glu | Ile | Pro | Ala | Glu | Asp | Ser | Ile | Lys | Val | Val |
| 1 | | | | 5 | | | | | 10 | | | | | 15 | |
| Cys | Arg | Phe | Arg | Pro | Leu | Asn | Asp | Ser | Glu | Glu | Lys | Ala | Gly | Ser | Lys |
| | | | 20 | | | | | 25 | | | | | 30 | | |
| Phe | Val | Val | Lys | Phe | Pro | Asn | Asn | Val | Glu | Glu | Asn | Cys | Ile | Ser | Ile |
| | | | 35 | | | | | 40 | | | | | 45 | | |
| Ala | Gly | Lys | Val | Tyr | Leu | Phe | Asp | Lys | Val | Phe | Lys | Pro | Asn | Ala | Ser |
| | | 50 | | | | | 55 | | | | | 60 | | | |
| Gln | Glu | Lys | Val | Tyr | Asn | Glu | Ala | Ala | Lys | Ser | Ile | Val | Thr | Asp | Val |
| 65 | | | | | 70 | | | | | 75 | | | | | 80 |
| Leu | Ala | Gly | Tyr | Asn | Gly | Thr | Ile | Phe | Ala | Tyr | Gly | Gln | Thr | Ser | Ser |
| | | | | 85 | | | | | 90 | | | | | 95 | |
| Gly | Lys | Thr | His | Thr | Met | Glu | Gly | Val | Ile | Gly | Asp | Ser | Val | Lys | Gln |
| | | | 100 | | | | | 105 | | | | | 110 | | |
| Gly | Ile | Ile | Pro | Arg | Ile | Val | Asn | Asp | Ile | Phe | Asn | His | Ile | Tyr | Ala |
| | | | 115 | | | | | 120 | | | | | 125 | | |
| Met | Glu | Val | Asn | Leu | Glu | Phe | His | Ile | Lys | Val | Ser | Tyr | Tyr | Glu | Ile |
| | | | 130 | | | | | 135 | | | | | 140 | | |
| Tyr | Met | Asp | Lys | Ile | Arg | Asp | Leu | Leu | Asp | Val | Ser | Lys | Val | Asn | Leu |
| 145 | | | | | 150 | | | | | 155 | | | | | 160 |
| Ser | Val | His | Glu | Asp | Lys | Asn | Arg | Val | Pro | Tyr | Val | Lys | Gly | Ala | Thr |
| | | | | 165 | | | | | 170 | | | | | 175 | |

| Glu | Arg | Phe | Val<br>180 | Ser | Ser | Pro | Glu<br>185 | Val | Phe | Glu | Val<br>190 | Ile | Glu | Glu |
|---|---|---|---|---|---|---|---|---|---|---|---|---|---|---|
| Gly | Lys | Ser<br>195 | Asn | Arg | His | Ile | Ala<br>200 | Val | Thr | Asn | Met<br>205 | Asn | Glu | His | Ser |
| Ser | Arg<br>210 | Ser | His | Ser | Val | Phe<br>215 | Leu | Ile | Asn | Val | Lys<br>220 | Gln | Glu | Asn | Leu |
| Glu<br>225 | Asn | Gln | Lys | Lys | Leu<br>230 | Ser | Gly | Lys | Leu | Tyr<br>235 | Leu | Val | Asp | Leu | Ala<br>240 |
| Gly | Ser | Glu | Lys | Val<br>245 | Ser | Lys | Thr | Gly | Ala<br>250 | Glu | Gly | Thr | Val | Leu<br>255 | Asp |
| Glu | Ala | Lys | Asn<br>260 | Ile | Asn | Lys | Ser | Leu<br>265 | Ser | Ala | Leu | Gly | Asn<br>270 | Val | Ile |
| Ser | Ala | Leu<br>275 | Ala | Asp | Gly | Asn | Lys<br>280 | Thr | His | Ile | Pro | Tyr<br>285 | Arg | Asp | Ser |
| Lys | Leu<br>290 | Thr | Arg | Ile | Leu | Gln<br>295 | Glu | Ser | Leu | Gly | Gly<br>300 | Asn | Ala | Arg | Thr |
| Thr<br>305 | Ile | Val | Ile | Cys | Cys<br>310 | Ser | Pro | Ala | Ser | Phe<br>315 | Asn | Glu | Ser | Glu | Thr<br>320 |
| Lys | Ser | Thr | Leu | Asp<br>325 | Phe | Gly | Arg | Arg | Ala<br>330 | Lys | Thr | Val | Lys | Asn<br>335 | Val |
| Val | Cys | Val | Asn<br>340 | Glu | Glu | Leu | Thr | Ala<br>345 | Glu | Glu | Trp | Lys | Arg<br>350 | Arg | Tyr |
| Glu | Lys | Glu<br>355 | Lys | Glu | Lys | Asn | Ala<br>360 | Arg | Leu | Lys | Gly | Lys<br>365 | Val | Glu | Lys |
| Leu | Glu<br>370 | Ile | Glu | Leu | Ala | Arg<br>375 | Trp | Arg | Ala | Gly | Glu<br>380 | Thr | Val | Lys | Ala |
| Glu<br>385 | Glu | Gln | Ile | Asn | Met<br>390 | Glu | Asp | Leu | Met | Glu<br>395 | Ala | Ser | Thr | Pro | Asn<br>400 |
| Leu | Glu | Val | Glu | Ala<br>405 | Ala | Gln | Thr | Ala | Ala<br>410 | Ala | Glu | Ala | Ala | Leu<br>415 | Ala |
| Ala | Gln | Arg | Thr<br>420 | Ala | Leu | Ala | Asn | Met<br>425 | Ser | Ala | Ser | Val | Ala<br>430 | Val | Asn |
| Glu | Gln | Ala<br>435 | Arg | Leu | Ala | Thr | Glu<br>440 | Cys | | | | | | | |

( 2 ) INFORMATION FOR SEQ ID NO:4:

( i ) SEQUENCE CHARACTERISTICS:
      ( A ) LENGTH: 411 amino acid residues
      ( B ) TYPE: amino acid
      ( D ) TOPOLOGY: linear ( x i ) SEQUENCE DESCRIPTION: SEQ ID NO:4:

| Met<br>1 | Ser | Ala | Glu | Arg<br>5 | Glu | Ile | Pro | Ala | Glu<br>10 | Asp | Ser | Ile | Lys | Val<br>15 | Val |
|---|---|---|---|---|---|---|---|---|---|---|---|---|---|---|---|
| Cys | Arg | Phe | Arg<br>20 | Pro | Leu | Asn | Asp | Ser<br>25 | Glu | Glu | Lys | Ala | Gly<br>30 | Ser | Lys |
| Phe | Val | Val<br>35 | Lys | Phe | Pro | Asn | Asn<br>40 | Val | Glu | Glu | Asn | Cys<br>45 | Ile | Ser | Ile |
| Ala | Gly<br>50 | Lys | Val | Tyr | Leu | Phe<br>55 | Asp | Lys | Val | Phe | Lys<br>60 | Pro | Asn | Ala | Ser |
| Gln<br>65 | Glu | Lys | Val | Tyr | Asn<br>70 | Glu | Ala | Ala | Lys | Ser<br>75 | Ile | Val | Thr | Asp | Val<br>80 |
| Leu | Ala | Gly | Tyr | Asn<br>85 | Gly | Thr | Ile | Phe | Ala<br>90 | Tyr | Gly | Gln | Thr | Ser<br>95 | Ser |
| Gly | Lys | Thr | His | Thr | Met | Glu | Gly | Val | Ile | Gly | Asp | Ser | Val | Lys | Gln |

|     |     |     |     |     | 100 |     |     |     |     | 105 |     |     |     |     | 110 |     |
|-----|-----|-----|-----|-----|-----|-----|-----|-----|-----|-----|-----|-----|-----|-----|-----|-----|

Gly Ile Ile Pro Arg Ile Val Asn Asp Ile Phe Asn His Ile Tyr Ala
            115             120                 125

Met Glu Val Asn Leu Glu Phe His Ile Lys Val Ser Tyr Tyr Glu Ile
    130                 135                 140

Tyr Met Asp Lys Ile Arg Asp Leu Leu Asp Val Ser Lys Val Asn Leu
145                 150                 155                 160

Ser Val His Glu Asp Lys Asn Arg Val Pro Tyr Val Lys Gly Ala Thr
                165                 170                 175

Glu Arg Phe Val Ser Ser Pro Glu Asp Val Phe Glu Val Ile Glu Glu
            180                 185                 190

Gly Lys Ser Asn Arg His Ile Ala Val Thr Asn Met Asn Glu His Ser
            195                 200                 205

Ser Arg Ser His Ser Val Phe Leu Ile Asn Val Lys Gln Glu Asn Leu
    210                 215                 220

Glu Asn Gln Lys Lys Leu Ser Gly Lys Leu Tyr Leu Val Asp Leu Ala
225                 230                 235                 240

Gly Ser Glu Lys Val Ser Lys Thr Gly Ala Glu Gly Thr Val Leu Asp
                245                 250                 255

Glu Ala Lys Asn Ile Asn Lys Ser Leu Ser Ala Leu Gly Asn Val Ile
            260                 265                 270

Ser Ala Leu Ala Asp Gly Asn Lys Thr His Ile Pro Tyr Arg Asp Ser
            275                 280                 285

Lys Leu Thr Arg Ile Leu Gln Glu Ser Leu Gly Gly Asn Ala Arg Thr
    290                 295                 300

Thr Ile Val Ile Cys Cys Ser Pro Ala Ser Phe Asn Glu Ser Glu Thr
305                 310                 315                 320

Lys Ser Thr Leu Asp Phe Gly Arg Arg Ala Lys Thr Val Lys Asn Val
            325                 330                 335

Val Cys Val Asn Glu Glu Leu Thr Ala Glu Glu Trp Lys Arg Arg Tyr
            340                 345                 350

Glu Lys Glu Lys Glu Lys Asn Ala Arg Leu Lys Gly Lys Val Glu Lys
    355                 360                 365

Leu Glu Ile Glu Leu Ala Arg Trp Arg Ala Gly Glu Thr Val Lys Ala
    370                 375                 380

Glu Glu Gln Ile Asn Met Glu Asp Leu Met Glu Ala Ser Thr Pro Asn
385                 390                 395                 400

Leu Glu Val Glu Ala Ala Gln Thr Ala Ala Cys
                405                 410

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

GAAGGCCTTG ACCCCTCCAA GGACTC 26

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear -continued (xi) SEQUENCE DESCRIPTION: SEQ ID NO:6:

GGAATTCAAT GATGATGATG ATGATGCTGA ACGGCGTCGA                40